(12) United States Patent
Jeschke et al.

(10) Patent No.: US 7,951,951 B2
(45) Date of Patent: May 31, 2011

(54) BICYCLIC ENAMINO(THIO)CARBONYL COMPOUNDS

(75) Inventors: Peter Jeschke, Bergisch Gladbach (DE); Robert Velten, Langenfeld (DE); Thomas Schenke, Bergisch Gladbach (DE); Michael Edmund Beck, Monheim (DE); Olga Malsam, Rösrath (DE); Udo Reckmann, Köln (DE); Ralf Nauen, Langenfeld (DE); Ulrich Görgens, Ratingen (DE); Leonardo Pitta, Leverkusen (DE); Christian Arnold, Langenfeld (DE); Erich Sanwald, Kiel (DE)

(73) Assignee: Bayer Cropscience AG, Monheim (DE)

( * ) Notice: Subject to any disclaimer, the term of this patent is extended or adjusted under 35 U.S.C. 154(b) by 174 days.

(21) Appl. No.: 12/295,151

(22) PCT Filed: Mar. 19, 2007

(86) PCT No.: PCT/EP2007/002393
§ 371 (c)(1),
(2), (4) Date: Jan. 24, 2009

(87) PCT Pub. No.: WO2007/115647
PCT Pub. Date: Oct. 18, 2007

(65) Prior Publication Data
US 2009/0181947 A1    Jul. 16, 2009

(30) Foreign Application Priority Data

Mar. 31, 2006  (DE) .................. 10 2006 015 456

(51) Int. Cl.
*C07D 211/68* (2006.01)
*C07D 265/04* (2006.01)
*A61K 31/535* (2006.01)

(52) U.S. Cl. .................. 546/193; 514/230.5; 544/88

(58) Field of Classification Search .................. 544/88; 514/230.5; 546/193
See application file for complete search history.

(56) References Cited

U.S. PATENT DOCUMENTS

| 7,186,829 | B1 | 3/2007 | Fischer et al. |
| 7,417,150 | B2 | 8/2008 | Jeschke et al. |
| 2004/0209896 | A1 | 10/2004 | Jeschke et al. |

FOREIGN PATENT DOCUMENTS

| EP | 0 284 174 | 9/1988 |
| EP | 0 373 464 | 6/1990 |
| EP | 0 383 453 | 10/1990 |
| EP | 0 446 913 | 9/1991 |
| EP | 0 539 588 | 5/1993 |
| EP | 0 569 947 | 11/1993 |
| EP | 0 775 700 | 5/1997 |
| EP | 0 780 384 | 6/1997 |
| EP | 0 794 180 | 9/1997 |
| JP | 05-239034 | 9/1993 |
| WO | WO 97/10226 | 3/1997 |
| WO | WO 98/33772 | 8/1998 |
| WO | WO 2004/082616 | 9/2004 |

OTHER PUBLICATIONS

International Search Report, App. No. PCT/EP2007/002393, dated Jul. 24, 2007 (4 pages).

*Primary Examiner* — Janet L Andres
*Assistant Examiner* — Heidi Reese
(74) *Attorney, Agent, or Firm* — Baker Donelson Bearman, Caldwell & Berkowitz, PC

(57) ABSTRACT

The present invention relates to novel bicyclic enamino(thio)carbonyl compounds, to processes for their preparation and to their use for controlling animal pests, especially arthropods, in particular insects.

15 Claims, No Drawings

BICYCLIC ENAMINO(THIO)CARBONYL COMPOUNDS

CROSS REFERENCE TO RELATED APPLICATIONS

This application is a §371 National Stage Application of PCT/EP2007/002393 filed Mar. 19, 2007 which claims priority from German Application 10 2006 015 456.8 filed Mar. 31, 2006.

BACKGROUND OF THE INVENTION

1. Field of the Invention

The present invention relates to novel bicyclic enamino (thio)carbonyl compounds, to processes for their preparation and to their use for controlling animal pests, especially arthropods, in particular insects.

2. Description of Related Art

The synthesis of specific bicyclic enaminocarbonyl systems is known (cf., for example, 5,6-dihydro-4H-furo[3,2-b]pyridin-2-one: Good, R. H. et al. J. Chem. Soc., Perkin Transactions 1: Organic and Bio-Organic Chemistry (1972-1999) (1972), (19), 2441-2445; Jones, G., Phipps, J. R. J, Chem. Soc., Perkin Transactions 1: Organic and Bio-Organic Chemistry (1972-1999) (1975), (20), 458-461; 5,6,7,7a-tetrahydro-4H-furo[3,2-b]pyridin-2-one: Good, R. H. et al. Tetrahedron Lett. (1972), 7, 609-612; 3-acetyl-5,6,7,7a-tetrahydro-6,6-dimethylfuro[3,2-b]pyridin-2-one: Brown, R. F. C. et al. Australian J. Chem. (1967), 20, 2485-97; 6,6a-dihydro-4-[2-(phenyl- or -hetaryl)ethyl]-2H-furo[3,2-b]pyrrole-2,5(4H)-dione: Lee, Y. S. et al., Synth. Commun. (1997), 27, 2799-2812).

SUMMARY OF THE INVENTION

Bicyclic enamino(thio)carbonyl compounds and their use as agents for controlling animal pests, especially arthropods, in particular insects, have hitherto not been disclosed.

This invention provides compounds of the formula (I)

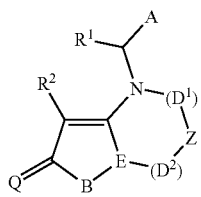

(I)

in which
A represents an optionally substituted aryl radical, heterocyclyl radical or represents a hetaryl radical from the group consisting of pyridyl, pyrimidinyl, pyridazinyl, pyrazinyl, triazinyl, pyrazolyl, thiophenyl, oxazolyl, isoxazolyl, oxadiazolyl, thiadiazolyl, isothiazolyl, imidazolyl, pyrrolyl, furanyl, thiazolyl, triazolyl which are optionally substituted by fluorine, chlorine, bromine, iodine, cyano, nitro, $C_1$-$C_4$-alkyl (which is optionally substituted by fluorine and/or chlorine), $C_1$-$C_3$-alkylthio (which is optionally substituted by fluorine and/or chlorine) or $C_1$-$C_3$-alkylsulphonyl which is optionally substituted by fluorine and/or chlorine),
B represents oxygen, sulphur, optionally substituted nitrogen or methylene,
E represents CH, C-alkyl or nitrogen,
$D^1$-Z-$D^2$ as a group together with the atoms linking them form an optionally substituted five-, six- or seven-membered ring which optionally comprises one or more heteroatoms,
$R^1$ represents hydrogen or alkyl,
$R^2$ represents hydrogen, alkyl, cycloalkyl, haloalkyl, nitro, cyano, formyl, carboxyl, alkoxycarbonyl, alkylcarbonyl, haloalkylcarbonyl, halogen,
Q represents oxygen or sulphur.

DETAILED DESCRIPTION OF A PREFERRED EMBODIMENT

Furthermore, it has been found that the novel substituted bicyclic enamino(thio)carbonyl compounds of the formula (I) are obtained when
a) according to preparation method 1
compounds of the general formula (II)

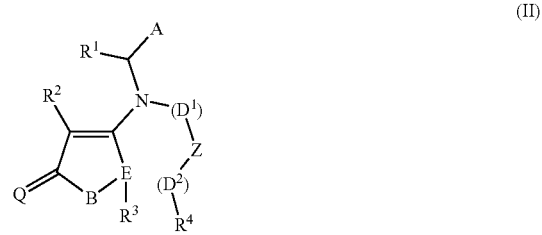

(II)

in which
Z preferably represents optionally substituted methylene,
$R^3$ preferably represents hydrogen or halogen, for example bromine, generated in situ,
$R^4$ preferably represents a suitable leaving group, for example halogen, or represents hydrogen, and
A, B, A, $R^1$, $R^2$, $D^1$, $D^2$, Q are as defined further above
are cyclized intramolecularly in the presence of a suitable basic reaction auxiliary and, if appropriate, in the presence of a suitable diluent, or when
b) according to preparation method 2
compounds of the general formula (III)

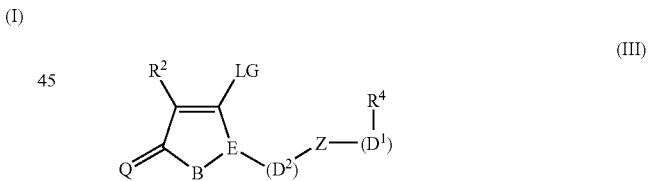

(III)

in which
Z preferably represents optionally substituted methylene,
LG represents a suitable leaving group, such as a secondary amino radical, hydroxyl, alkoxy or alkylthio,
B, E, $R^2$, $D^1$, $D^2$, Q are as defined further above,
$R^4$ represents a suitable leaving group, for example halogen,
are, in a first reaction step, reacted with compounds of the general formula (IV)

(IV)

in which

A and $R^1$ are as defined further above in the presence of a suitable basic reaction auxiliary and, if appropriate, in the presence of a suitable diluent, to give compounds of the general formula (V)

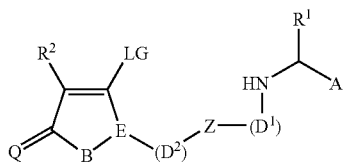
(V)

in which

Z preferably represents optionally substituted methylene,

LG represents a suitable leaving group, for example a secondary amino radical, hydroxyl, alkoxy or alkylthio, A, B, E, $R^1$, $R^2$, $D^1$, $D^2$, Q are as defined further above, and these are then, in a second reaction step, cyclized intramolecularly in the presence of a suitable acidic reaction auxiliary and, if appropriate, in the presence of a suitable diluent, or when c) according to preparation method 3
compounds of the general formula (VI)

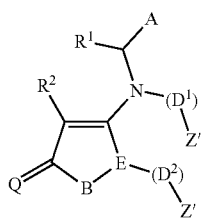
(VI)

in which

Z' preferably represents an unsaturated carbon-carbon bond,

A, B, E, $R^1$, $R^2$, $D^1$, $D^2$, Q are as defined further above are reacted in the presence of a suitable catalyst and, if appropriate, in the presence of a suitable diluent, or when d) according to preparation method 4
compounds of the general formula (VII)

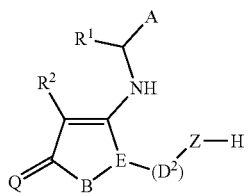
(VII)

in which

Z preferably represents a heteroatom from the group consisting of oxygen, sulphur, nitrogen, A, B, $R^1$, $R^2$, $D^2$, Q are as defined further above are reacted with compounds of the general formula (VIII) or (IX)

 H—CO—R' (VIII) or

 (—O—CHR'—)$_n$ (IX)

in which

R' represents hydrogen or $C_1$-$C_4$-alkyl, n represents ≦3, if appropriate in the presence of an acidic reaction auxiliary and if appropriate in the presence of a diluent.

Finally, it has been found that the novel compounds of the formula (I) have strongly pronounced biological properties and are suitable especially for controlling animal pests, in particular insects, arachnids and nematodes, encountered in agriculture, in forests, in the protection of stored products and in the protection of materials and also in the hygiene sector.

Depending on the nature of the substituents, the compounds of the formula (I) may, if appropriate, be present as geometrical and/or optically active isomers or corresponding isomer mixtures of varying composition. The invention relates both to the pure isomers and to the isomer mixtures.

The formula (I) provides a general definition of the compounds according to the invention.

Preferred substituents or ranges of the radicals given in the formulae mentioned above and below are illustrated below.

A preferably represents tetrahydrofuryl or represents pyrid-3-yl, which is optionally substituted in the 6-position by halogen, $C_1$-$C_4$-alkyl or $C_1$-$C_4$-haloalkyl, pyrimidin-5-yl which is optionally substituted in the 2-position by halogen or $C_1$-$C_4$-alkyl, 1H-pyrazol-4-yl, optionally substituted in the 1-position by $C_1$-$C_4$-alkyl and in the 3-position by halogen, 1H-pyrazol-5-yl, optionally substituted in the 3-position by halogen or $C_1$-$C_4$-alkyl, isoxazol-5-yl, optionally substituted in the 3-position by halogen or $C_1$-$C_4$-alkyl, 1,2,4-oxadiazol-5-yl, optionally substituted in the 3-position by halogen or $C_1$-$C_4$-alkyl, 1-methyl-1,2,4-triazol-3-yl, 1,2,5-thiadiazol-3-yl, 1,3-thiazolyl-5-yl, optionally substituted in the 2-position by halogen or $C_1$-$C_4$-alkyl.

Furthermore

A preferably represents a radical

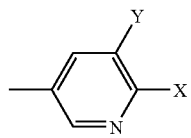

in which

X represents halogen, $C_1$-$C_4$-alkyl, $C_1$-$C_4$-haloalkyl,

Y represents halogen, $C_1$-$C_4$-alkyl, $C_1$-$C_4$-haloalkyl, $C_1$-$C_4$-haloalkoxy, azido and cyano; in particular, A represents a radical from the group consisting of 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl, 5-difluoromethyl-6-iodopyrid-3-yl.

B preferably represents oxygen or methylene.

$D^1$-Z-$D^2$ as a group preferably represents an optionally halogen-, oxo-, hydroxyl-, $C_1$-$C_4$-alkyl- or $C_1$-$C_4$-alkylene- substituted saturated or unsaturated $C_2$-$C_4$-group in which optionally one carbon atom may be replaced by a heteroatom from the group consisting of oxygen, sulphur and nitrogen.

$R^1$ preferably represents hydrogen.

$R^2$ preferably represents hydrogen, alkyl or halogen (where halogen represents in particular fluorine or chlorine).

Q preferably represents oxygen.

A particularly preferably represents a radical from the group consisting of 6-chloropyrid-3-yl, 6-bromopyrid-3-yl, 6-methylpyrid-3-yl, 6-trifluoromethylpyrid-3-yl, 2-methylpyrimidin-5-yl, 2-chloropyrimid-5-yl, 1H-pyrazol-4-yl, which is optionally substituted in the 1-position by methyl or ethyl and in the 3-position by chlorine, 1H-pyrazol-5-yl, 3-methylpyrazol-5-yl, 2-bromo-1,3-thiazol-5-yl, 2-chloro-1,3-thiazol-5-yl, isoxazol-5-yl which is optionally substituted in the 3-position by methyl, ethyl, chlorine or bromine, 3-methyl-1,2,4-oxadiazol-5-yl, 1-methyl-1,2,4-triazol-3-yl, 1,2,5-thiadiazol-3-yl.

A furthermore particularly preferably represents a radical from the group consisting of 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-methyl-6-iodopyrid-3-yl or 5-difluoromethyl-6-chloropyrid-3-yl.

B particularly preferably represents oxygen or methylene.

$D^1$-Z-$D^2$ as a group particularly preferably represents an optionally $C_1$-$C_2$-alkyl- or $C_1$-$C_2$-alk-ylene-substituted saturated or unsaturated $C_2$-$C_3$-group in which one carbon atom may be replaced by a heteroatom from the group consisting of oxygen, sulphur and nitrogen, in particular —$CH_2$—$CH_2$—, —HC=CH—, —$CH_2$—$CH_2$—$CH_2$—, —$CH_2$—C(=$CH_2$)—$CH_2$—, —$CH_2$—CO—$CH_2$—, —$CH_2$—CH(OH)—$CH_2$—, —$CH_2$—$CF_2$—$CH_2$—, —$CH_2$—CHF—$CH_2$—, —$CH_2$—CHCl—$CH_2$—, —CH=CH—$CH_2$—, —$CH_2$—$CH_2$—CH=, —$CH_2$—$CH_2$—CH(OH)—, —$CH_2$—CH($CH_3$)—$CH_2$—, —$CH_2$—$CH_2$—$CH_2$—$CH_2$—, —$CH_2$—CH=CH—$CH_2$—, —$CH_2$—O—$CH_2$—, —$CH_2$—$CH_2$—O—, —$CH_2$—N($CH_3$)—$CH_2$—, —$CH_2$—$CH_2$—N($CH_3$)— or —$CH_2$—S—$CH_2$—.

$R^1$ particularly preferably represents hydrogen.

$R^2$ particularly preferably represents hydrogen, fluorine or chlorine.

Q particularly preferably represents oxygen.

A very particularly preferably represents a radical from the group consisting of 6-chloropyrid-3-yl, 6-bromopyrid-3-yl, 2-chloropyrimid-5-yl, 5-fluoro-6-chloropyrid-3-yl, 5,6-dichloropyrid-3-yl, 5-fluoro-6-bromopyrid-3-yl, 2-chloro-1,3-thiazol-5-yl.

B very particularly preferably represents oxygen.

$D^1$-$D^2$ as a group very particularly preferably represents —$CH_2$—$CH_2$—$CH_2$—, —$CH_2$—C(=$CH_2$)—$CH_2$—, —$CH_2$—C($CH_3$)—$CH_2$—, —$CH_2$—$CH_2$—$CH_2$—$CH_2$—, —$CH_2$—CH=CH—$CH_2$—, —$CH_2$—O—$CH_2$—, —$CH_2$—$CH_2$—O—, —$CH_2$—CHF—$CH_2$—, —$CH_2$—CHCl—$CH_2$—, —CH=CH—$CH_2$—, —$CH_2$—$CH_2$—CH= or —$CH_2$—$CH_2$—CH(OH)—.

$R^1$ very particularly preferably represents hydrogen.

$R^2$ very particularly preferably represents hydrogen.

Q very particularly preferably represents oxygen.

In a special group of compounds of the formula (I), $D^1$-Z-$D^2$ represents —$CH_2$—$CH_2$—

In a further special group of compounds of the formula (I), $D^1$-Z-$D^2$ represents —HC=CH—.

In a further special group of compounds of the formula (I), $D^1$-Z-$D^2$ represents —$CH_2$—$CH_2$—$CH_2$—

In a further special group of compounds of the formula (I), $D^1$-Z-$D^2$ represents —$CH_2$—C(=$CH_2$)—$CH_2$—.

In a further special group of compounds of the formula (I), $D^1$-Z-$D^2$ represents —$CH_2$—O—$CH_2$—.

In a further special group of compounds of the formula (I), $D^1$-Z-$D^2$ represents —$CH_2$—$CH_2$—O—.

In a further special group of compounds of the formula (I), $D^1$-Z-$D^2$ represents —$CH_2$—N($CH_3$)—$CH_2$—.

In a further special group of compounds of the formula (I), $D^1$-Z-$D^2$ represents —$CH_2$—$CH_2$—CH=.

In a further special group of compounds of the formula (I), $D^1$-Z-$D^2$ represents —$CH_2$—$CH_2$—CH(OH)—.

In a further special group of compounds of the formula (I), $D^1$-Z-$D^2$ represents —$CH_2$—CHF—$CH_2$—

In a further special group of compounds of the formula (I), $D^1$-Z-$D^2$ represents —$CH_2$—CHCl—$CH_2$—.

In a further special group of compounds of the formula (I), A represents 6-chloropyridin-3-yl

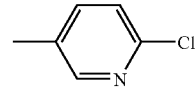

In a further special group of compounds of the formula (I), A represents 6-bromopyridin-3-yl

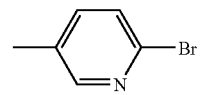

In a further special group of compounds of the formula (I), A represents 2-chloropyrimidin-5-yl

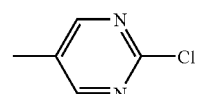

In a further special group of compounds of the formula (I), A represents 5-fluoro-6-chloropyrid-3-yl

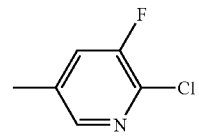

In a further special group of compounds of the formula (I), A represents 2-chloro-1,3-thiazol-5-yl

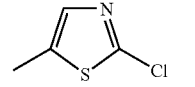

In a further special group of compounds of the formula (I), A represents 5,6-dichloropyrid-3-yl

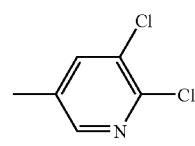

In a further special group of compounds of the formula (I), A represents 5-bromo-6-chloropyrid-3-yl

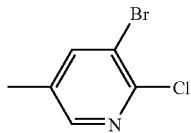

In a further special group of compounds of the formula (I), A represents 5-methyl-6-chloropyrid-3-yl

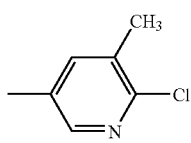

In a further special group of compounds of the formula (I), A represents 5-fluoro-6-bromopyrid-3-yl

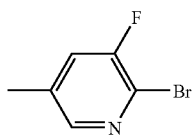

In a further special group of compounds of the formula (I), A represents 5-chloro-6-bromopyrid-3-yl

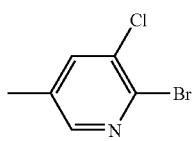

In a further special group of compounds of the formula (I), A represents 5-chloro-6-iodopyrid-3-yl

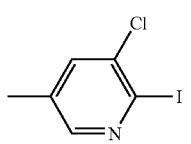

In a further special group of compounds of the formula (I), $R^1$ and $R^2$ represent hydrogen, E represents carbon, B and Q represent oxygen, A represents 6-chloropyrid-3-yl

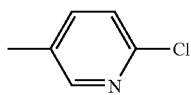

In a further special group of compounds of the formula (I), $R^1$ and $R^2$ represent hydrogen, E represents carbon, B and Q represent oxygen, A represents 6-bromopyrid-3-yl

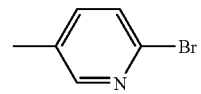

In a further special group of compounds of the formula (I), $R^1$ and $R^2$ represent hydrogen, E represents carbon, B and Q represent oxygen, A represents 2-chloropyrimidin-5-yl

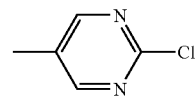

In a further special group of compounds of the formula (I), $R^1$ and $R^2$ represent hydrogen, E represents carbon, B and Q represent oxygen, A represents 5-fluoro-6-chloropyrid-3-yl

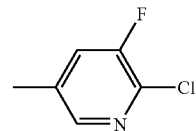

In a further special group of compounds of the formula (I), $R^1$ and $R^2$ represent hydrogen, E represents carbon, B and Q represent oxygen, A represents 2-chloro-1,3-thiazol-5-yl

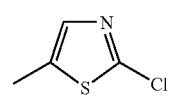

In a further special group of compounds of the formula (I), $R^1$ and $R^2$ represent hydrogen, E represents carbon, B and Q represent oxygen, A represents 5,6-dichloropyrid-3-yl

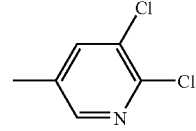

In a further special group of compounds of the formula (I), $R^1$ and $R^2$ represent hydrogen, E represents carbon, B and Q represent oxygen, A represents 5-bromo-6-chloropyrid-3-yl

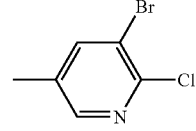

In a further special group of compounds of the formula (I), $R^1$ and $R^2$ represent hydrogen, E represents carbon, B and Q represent oxygen, A represents 5-methyl-6-chloropyrid-3-yl

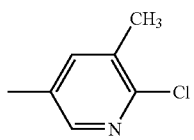

In a further special group of compounds of the formula (I), $R^1$ and $R^2$ represent hydrogen, E represents carbon, B and Q represent oxygen, A represents 5-fluoro-6-bromopyrid-3-yl

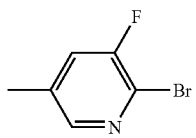

In a further special group of compounds of the formula (I), $R^1$ and $R^2$ represent hydrogen, E represents carbon, B and Q represent oxygen, A represents 5-chloro-6-bromopyrid-3-yl

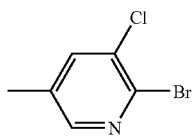

In a further special group of compounds of the formula (I), $R^1$ and $R^2$ represent hydrogen, E represents carbon, B and Q represent oxygen, A represents 5-chloro-6-iodopyrid-3-yl

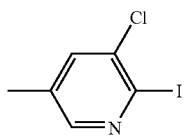

In a further special group of compounds of the formula (I), $R^1$ and $R^2$ represent hydrogen, $D^1$-Z-$D^2$ represents —(CH$_2$)$_3$—, E represents carbon, B and Q represent oxygen, A represents 6-chloropyrid-3-yl

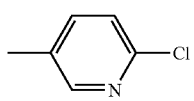

In a further special group of compounds of the formula (I), $R^1$ and $R^2$ represent hydrogen, $D^1$-Z-$D^2$ represents —(CH$_2$)$_3$—, E represents carbon, B and Q represent oxygen, A represents 6-bromopyrid-3-yl

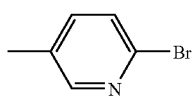

In a further special group of compounds of the formula (I), $R^1$ and $R^2$ represent hydrogen, $D^1$-Z-$D^2$ represents —(CH$_2$)$_3$—, E represents carbon, B and Q represent oxygen, A represents 2-chloropyrimidin-5-yl

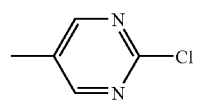

In a further special group of compounds of the formula (I), $R^1$ and $R^2$ represent hydrogen, $D^1$-Z-$D^2$ represents —(CH$_2$)$_3$—, E represents carbon, B and Q represent oxygen, A represents 5-fluoro-6-chloropyrid-3-yl

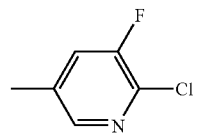

In a further special group of compounds of the formula (I), $R^1$ and $R^2$ represent hydrogen, $D^1$-Z-$D^2$ represents —(CH$_2$)$_3$—, E represents carbon, B and Q represent oxygen, A represents 2-chloro-1,3-thiazol-5-yl

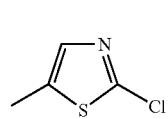

In a further special group of compounds of the formula (I), $R^1$ and $R^2$ represent hydrogen, $D^1$-Z-$D^2$ represents —(CH$_2$)$_3$—, E represents carbon, B and Q represent oxygen, A represents 5,6-dichloropyrid-3-yl

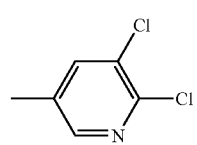

In a further special group of compounds of the formula (I), $R^1$ and $R^2$ represent hydrogen, $D^1$-Z-$D^2$ represents —(CH$_2$)$_3$—, E represents carbon, B and Q represent oxygen, A represents 5-bromo-6-chloropyrid-3-yl

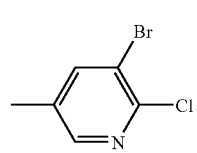

In a further special group of compounds of the formula (I), $R^1$ and $R^2$ represent hydrogen, $D^1$-Z-$D^2$ represents —(CH$_2$)$_3$—, E represents carbon, B and Q represent oxygen, A represents 5-methyl-6-chloropyrid-3-yl

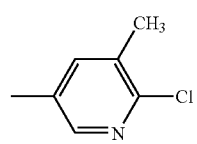

In a further special group of compounds of the formula (I), $R^1$ and $R^2$ represent hydrogen, $D^1$-Z-$D^2$ represents —$(CH_2)_3$—, E represents carbon, B and Q represent oxygen, A represents 5-fluoro-6-bromopyrid-3-yl

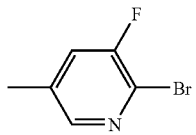

In a further special group of compounds of the formula (I), $R^1$ and $R^2$ represent hydrogen, $D^1$-Z-$D^2$ represents —$(CH_2)_3$—, E represents carbon, B and Q represent oxygen, A represents 5-chloro-6-bromopyrid-3-yl

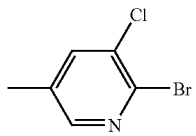

In a further special group of compounds of the formula (I), $R^1$ and $R^2$ represent hydrogen, $D^1$-Z-$D^2$ represents —$(CH_2)_3$—, E represents carbon, B and Q represent oxygen, A represents 5-chloro-6-iodopyrid-3-yl

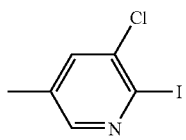

The general or preferred radical definitions or illustrations given above apply both to the end products and, correspondingly, to the starting materials and intermediates. These radical definitions can be combined with one another as desired, i.e. including combinations between the respective preferred ranges.

Preference according to the invention is given to the compounds of the formula (I) which contain a combination of the meanings listed above as being preferred.

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

If, in the process 1 according to the invention for preparing the novel compounds of the formula (I), the compound of the formula (II) used is, for example, 2-{[(6-chloropyridin-3-yl)methyl]amino}ethanol (route A) or 4-[[(6-chloropyridin-3-yl)methyl](3-iodopropyl)amino]-furan-2(5H)-one (route B), the preparation process 1 can be represented by the reaction scheme I below:

Scheme I

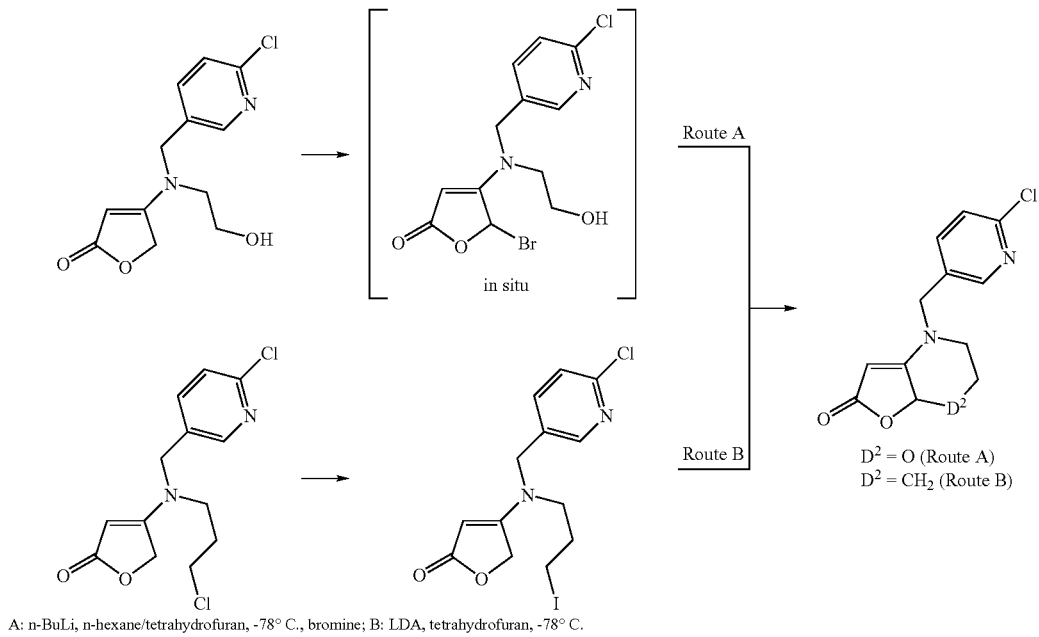

A: n-BuLi, n-hexane/tetrahydrofuran, -78° C., bromine; B: LDA, tetrahydrofuran, -78° C.

The formula (II) provides a general definition of the compounds required as starting materials for carrying out the process I according to the invention.

In this formula (II), A, B, E, Z, $R^1$, $R^2$, $R^3$, $R^4$, $D^1$, $D^2$, Q preferably represent those radicals which have already been mentioned in connection with the description of the compounds of the formula (I) according to the invention as preferred substituents.

The compounds of the general formula (II) can be obtained by methods known from the literature (for example EP 0539588 A1) according to reaction scheme II

Scheme II

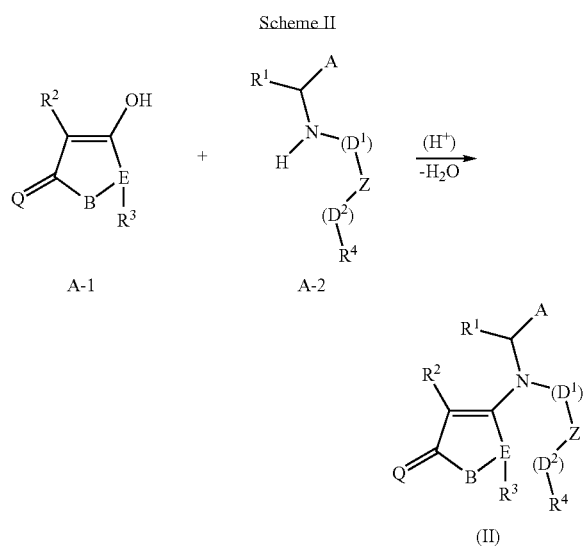

Suitable starting materials (A-1) for preparing the compounds of the general formula (II) are tetronic acids (B, Q=oxygen, E-R³=CH—R³ (Said, A. Specialty Chemicals Magazine (1984), 4(4), 7-8; Rao, Y. S. Chem. Rev. (1976), 76, 625-694; Tejedor, D.; Garcia-Tellado, F. Org. Preparations and Procedures International (2004), 36, 35-59; Reviews); B represents sulphur and Q represents oxygen: thiotetronic acids (Thomas, E. J. Special Publication—Royal Society of Chemistry (1988), 65 (Top. Med. Chem.), 284-307, Review), B represents methylene and Q represents oxygen: cyclopentane-1,3-diones (Schick, Hans; Eichhorn, Inge. Synthesis (1989), (7), 477-492, Review).

Further suitable starting materials (A-2) for preparing the compounds of the general formula (II) are secondary amines (D¹=optionally substituted carbon), N,O-disubstituted hydroxylamines (D¹=oxygen) or N,N'-disubstituted hydrazines (D¹=optionally substituted nitrogen). These starting materials can be obtained by methods known from the literature (cf., for example, S. Patai "The Chemistry of Amino Group", Interscience Publishers, New York, 1968).

Some aminoxy compounds acting as starting components for the compounds (A-2; D¹=oxygen) are commercially available, and they can be obtained by known methods. A general route for preparing aminoxy compounds consists, for example, in reacting a hydroxylamine derivative which has a protective group (PG) on nitrogen (for example R" and R'" together: phthaloyl, isopropylidene, α-hydroxybenzylidene group) with a compound R$^{iv}$-LG (O-alkylation; R$^{iv}$ represents optionally substituted alkyl) in a diluent, followed by removal of the respective protective group. In compound R$^{iv}$-LG, R$^{iv}$ is as defined above and LG represents a nucleofugic leaving group, for example aliphatically or aromatically substituted sulphonyloxy, e.g. methanesulphonyloxy (MesO=mesyloxy), salts of sulphonic acid, para-toluene-sulphonyloxy (TosO=tosyloxy), and furthermore also, for example, halogen, in particular bromine, chlorine or iodine (cf. O-alkylation). The preparation of aminoxy compounds is shown in reaction scheme III below:

Scheme III

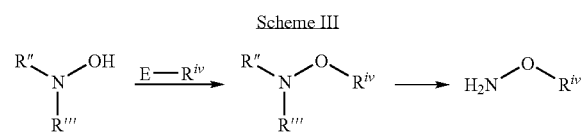

Alternatively, when hydroxy compounds (R$^{iv}$—OH) are used, it is possible, for example, to carry out an intramolecular dehydratization reaction. Particularly suitable for this purpose is a variant of the Mitsunobu reaction (O. Mitsunobu et al., Synthesis 1981, 1-28) where the hydroxyl compound is reacted with N-protected hydroxylamine derivatives, such as, for example, N-hydroxyphthalimide, N-hydroxy-5-norbornene-2,3-dicarboximide or ethyl acethydroxamate, and, for example, triphenylphosphine and diethyl N,N'-azodicarboxylate.

The release of the aminoxy compounds can be carried out under conditions known from the literature, expediently in the following manner: the hydrazinolysis is preferably carried out in a diluent, for example alcohol, at boiling point. The hydrolysis is preferably carried out in an aqueous, aqueous-alcoholic or alcoholic solution by heating for a number of hours. If R" and R'" together represent an isopropylidene group, acidic hydrolysis may be employed, and if R" and R'" together represent an α-hydroxybenzylidene group or R'" represents a carbethoxy group, either alkaline or acidic hydrolysis may be employed.

For preparing the starting materials (A-2), it is advantageous to react, for example, compounds of the general formula (A-3) in which A is as defined above and LG represents a suitable leaving group (for example chlorine, bromine, iodine, O-tosyl, O-mesyl) with compounds of the general formula (A-4), in which R represents the radical (D¹)-Z-(D²)-R⁴ in which D¹, D² and R⁴ are as defined further above, if appropriate in the presence of diluents and if appropriate in the presence of the basic reaction auxiliaries mentioned in preparation process 2 (cf. scheme III).

Scheme III

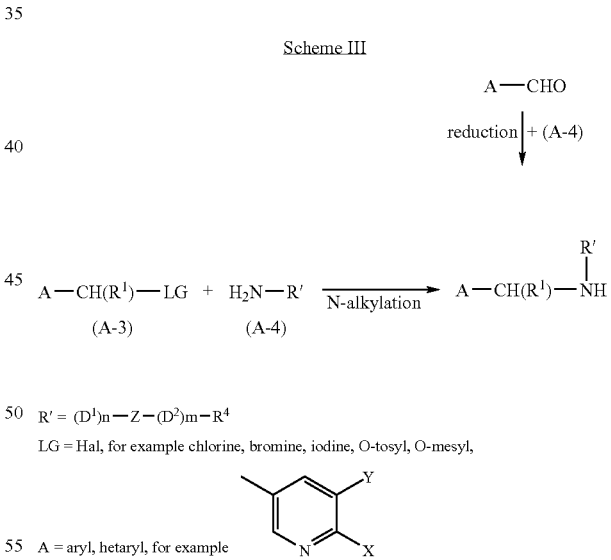

A = aryl, hetaryl, for example 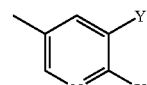

However, alternatively and in certain cases it is also possible to prepare starting materials (A-2) in which R¹ represents hydrogen from the corresponding aldehydes (A-CHO) and the compounds (A-4) by reductive amination (cf. Houben-Weyl, Methoden der Organischen Chemie [Methods of Organic Chemistry], Vol. XI/1, Georg Thieme Verlag Stuttgart, p. 602).

General routes for preparing the starting materials (A-3) are shown in reaction scheme IV.

Scheme IV

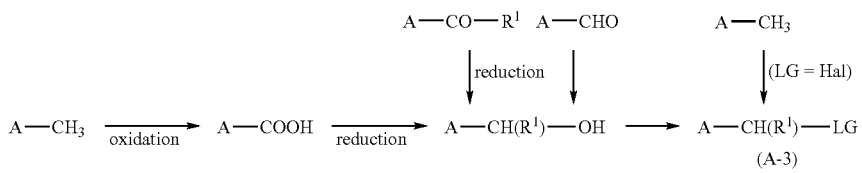

LG = Hal, for example chlorine, bromine, iodine, O-tosyl, O-mesyl,

A = aryl, hetaryl, for example 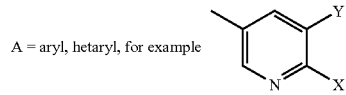

Some of the compounds (A-3, $R^1$=hydrogen) are commercially available, some are known, or they can be obtained by known methods (for example 2-chloro-5-chloromethyl-1,3-thiazole: DE 3 631 538 (1988), EP 446 913 (1991), EP 780 384 (1997), EP 775 700 (1997), EP 794 180 (1997), WO 9 710 226 (1997); 6-chloro-3-chloromethylpyridine: DE 3 630 046 A1 (1988), EP 373 464 A2 (1990), EP 373 464 A2 (1990), EP 393 453 A2 (1990), EP 569 947 A1 (1993); 6-chloro-3-bromomethylpyridine: I. Cabanal-Duvillard et al., Heterocycl. Commun. 5, 257-262 (1999); 6-bromo-3-chloromethylpyridine, 6-bromo-3-hydroxymethylpyridine: U.S. Pat. No. 5,420,270 A (1995); 6-fluoro-3-chloromethylpyridine: J. A. Pesti et al., J. Org. Chem. 65, 7718-7722 (2000); 2-methyl-3-chloromethylpyridine: EP 302 389 A2 (1989); 2-trifluoromethyl-3-chloromethyl-pyridine: WO 2004082616 A2 (2004); 3-chloro-6-chloromethylpyridazine: EP 284 174 A1 (1988); 2-chloro-5-pyrazinylmethyl chloride: J. Heterocycl. Chem. 23, 149-151 (1986); 2-chloro-5-pyrazinylmethyl bromide: JP 05 239 034 A2 (1993).

Methyl-substituted aromatic or heterocyclic compounds (A-CH₃) can be converted, for example, by oxidation into corresponding aromatic or heterocyclic carboxylic acids (A-COOH, for example 5-fluoro-6-bromonicotinic acid: F. L. Setliff, G. O. Rankin, J. Chem. Eng. Data (1972), 17, 515-516; 5-chloro-6-bromonicotinic acid and 5,6-dibromonicotinic acid: F. L. Setliff et al., J. Chem. Eng. Data (1981), 26, 332-333; 5-iodo-6-bromonicotinic acid: F. L. Setliff et al., J. Chem. Eng. Data (1978), 23, 96-97; 5-fluoro-6-iodonicotinic acid and 5-bromo-6-iodonicotinic acid: F. L. Setliff et al., J. Chem. Eng. Data (1973), 18, 449-450; 5-chloro-6-iodonicotinic acid: F. L. Setliff, J. E. Lane J. Chem. Eng. Data (1976), 21, 246-247) or carboxylic esters (for example methyl 5-methyl-6-fluoronicotinate: WO 9833772 A1, 1998; methyl 5-methyl-6-bromonicotinate: WO 9730032 A1, 1997). Also described in the prior art is the synthesis of formyl group-containing aromatic or heterocyclic compounds (A-CHO, for example 6-chloro-3-formyl-5-methylpyridine: DE 4429465 A1, 1996) from non-cyclic starting components; this can be achieved, for example, by 1,3-dipolar cycloaddition (for example: 5-chloromethyl-3-bromoisoxazole: P. Pevarello, M. Varasi Synth. Commun. (1992), 22, 1939-1948).

The aromatic or heteroaromatic cyclic carboxylic acids (A-COOH) or alkylcarbonyl compounds (A-CO—$R^1$; $R^1$=alkyl) can then be converted by methods known from the literature into the corresponding aromatic or heterocyclic hydroxyalkyl compounds (A-CH($R^1$)—OH; $R^1$=H, alkyl) which are then converted by methods known from the literature into activated aromatic or heterocyclic hydroxymethyl compounds (A-CH($R^1$)-LG, LG=O-tosyl, O-mesyl) or aromatic or heterocyclic halomethyl compounds (A-CH($R^1$)-LG, LG=Hal). The latter can also be obtained from the corresponding methyl group-containing aromatic or heterocyclic compounds (A-CH₃) using suitable halogenating agents known from the literature. Examples for this procedure which may be mentioned are the synthesis of the halomethyl-substituted heterocycles: 5-chloromethyl-2-methylpyrimidine (U. Eiermann et al., Chem. Ber. (1990), 123, 1885-9); 3-chloromethyl-5-bromo-6-chloropyridine, 3-bromo-5-iodo-6-chloropyridine (S. Kagabu et al., J. Pestic. Sci. (2005), 30, 409-413).

Starting materials (A-10) in which A represents a 5,6-disubstituted pyrid-3-yl radical can also be obtained by methods known from the literature. Suitable starting materials known from the literature are, for example, the 6-halo-substituted 5-nitro-β-picolines (A-5) which can be modified according to known literature procedures, as shown in reaction scheme V.

Scheme V

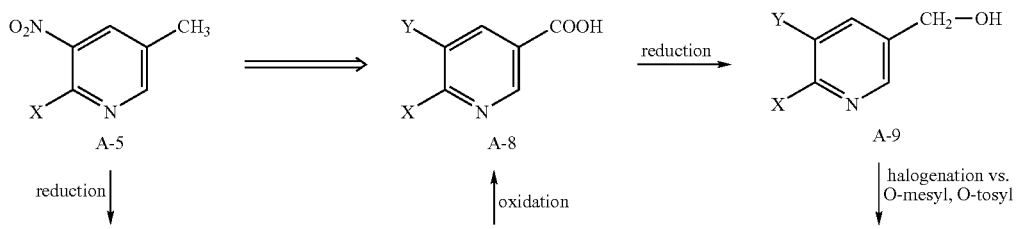

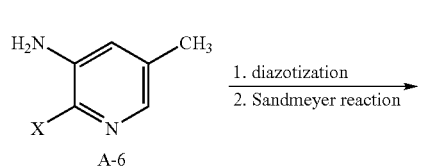 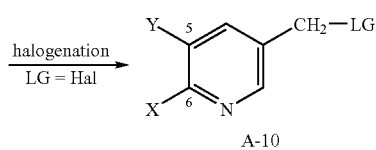

X, Y = halogen, for example fluorine, chlorine, bromine, iodine
LG = halogen, O-mesyl, O-tosyl, The reduction of the nitro group in 6-halo-substituted 5-nitro-β-picolines (A-5), for example, gives 6-halo-substituted 5-amino-β-picolines (A-6, for example 5-amino-6-chloro-β-picoline and 5-amino-6-bromo-β-picoline: Setliff, F. L. Org. Preparations and Preparations Int. (1971), 3, 217-222; Kagabu, S. et al. J. Pestic. Sci. (2005), 30, 409-413). Subsequent diazotization and Sandmeyer reaction (C. F. H. Allen, J. R. Thirtle, Org. Synth., Coll. Vol. III, 1955, p. 136) allows the introduction of halogen substituents in the 5-position (A-7, for example 5-fluoro-6-chloro-β-picoline and 5-fluoro-6-bromo-β-picoline: Setliff, F. L. Org. Preparations and Preparations Int. (1971), 3, 217-222; 5-iodo-6-chloro-β-picoline: Kagabu, S. et al. J. Pestic. Sci. (2005), 30, 409-413; 5,6-dichloropicoline: Setliff, F. L.; Lane, J. E. J. Chem. Engineering Data (1976), 21, 246-247). The oxidation of the methyl group in the 5,6-disubstituted β-picolines (A-7) then leads to the corresponding 5,6-disubstituted nicotinic acids (A-8, for example 5-fluoro-6-chloronicotinic acid and 5-fluoro-6-bromonicotinic acid: Setliff F. L., Rankin G. O. J. Chem. Engineering Data (1972), 17, 515-516; 5-bromo-6-fluoronicotinic acid, 5-bromo-6-chloronicotinic acid and 5-bromo-6-bromonicotinic acid: F. L. Setliff J. Chem. Engineering Data (1970), 15, 590-591; 5-chloro-6-bromonicotinic acid and 5-iodo-6-bromonicotinic acid: Setliff, F. L., Greene, J. S. J. Chem. Engineering Data (1978), 23, 96-97; also known is 5-chloro-6-trifluoromethylnicotinic acid: F. Cottet et al., Synthesis (2004), 10, 1619-1624), which can be converted in the presence of reducing agents into the corresponding hydroxymethylated pyridines (A-9) (for example 5-bromo-6-chloro-3-hydroxymethylpyridine: Kagabu, S. et al., J. Pestic. Sci. (2005), 30, 409-413).

In 6-chloro-5-nitronicotinic acid (A-8, X=Cl, Y=NO₂; Boyer, J. H.; Schoen, W., J. Am. Chem. Soc. (1956), 78, 423-425), it is possible to form, by reduction, 6-chloro-3-hydroxymethyl-5-nitropyridine (A-9, X=Cl, Y=NO₂; Kagabu, S. et al., J. Med. Chem. (2000), 43, 5003-5009) which is then reduced to give 6-chloro-3-hydroxymethyl-5-aminopyridine (A-9, X=Cl, Y=NH₂; Kagabu, S. et al., J. Med. Chem. (2000), 43, 5003-5009) and, via diazotization and reaction with hydroxylamine, converted into 6-chloro-3-hydroxymethyl-5-azidopyridine (A-9, X=Cl, Y=N₃; Kagabu, S. et al., J. Med. Chem. (2000), 43, 5003-5009). Subsequent halogenation with thionyl chloride gives 6-chloro-3-chloromethyl-5-azidopyridine (VII, X=Cl, Y=N₃, LG=Cl; Kagabu, S. et al., J. Med. Chem. (2000), 43, 5003-5009).

Alternatively, halogenation of the methyl group in the 3-position of (A-7) gives the compounds (A-10) in which LG represents halogen (for example: 3-bromomethyl-6-chloro-5-fluoropyridine, 3-bromomethyl-6-chloro-5-iodopyridine: Kagabu, S. et al. J. Pestic. Sci. (2005), 30, 409-413). When 6-halo-substituted 5-nitro-β-picolines (A-7; Y=NO₂) are used, there may be initial halogenation of the methyl group in the 3-position (for example 3-bromomethyl-6-chloro-5-nitropyridine: Kagabu, S. et al., J. Pestic. Sci. (2005), 30, 409-413). If appropriate, the nitro group may also be reduced at a later stage in the reaction sequence.

Also known from the literature is the introduction of substituents in the 5-position (for example Y=N₃) of compounds (A-10) in which LG represents N-morpholino. This radical can subsequently easily be replaced by halogen (LG=Hal) (cf. S. Kagabu et al., J. Med. Chem. 2000, 43, 5003-5009; reaction conditions: ethyl chloroformate, tetrahydrofuran, 60° C.).

In general, it is possible to replace halogen atoms in the vicinity of the pyridine nitrogen by other halogen atoms or halogenated groups such as, for example, trifluoromethyl (transhalogenation, for example: chlorine for bromine or iodine; bromine for iodine or fluorine; iodine for fluorine or trifluoromethyl). Thus, a further alternative synthesis route entails exchange of the halogen atom (for example X=Cl) in the 6-position of the pyrid-5-yl radical (for example in A-8 where X, Y=Cl; 5,6-dichloronicotinic acid: Setliff, F. L.; Lane, J. E. J. Chem. Engineering Data (1976), 21, 246-247) for another halogen atom, for example iodine or fluorine (for example: A-8 where X=I; 5-bromo-6-iodonicotinic acid and A-8 where X=F; 5-bromo-6-fluoronicotinic acid: Setliff, F. L.; Price, D. W. J. Chem. Engineering Data (1973), 18, 449-450). However, this transhalogenation may also, if appropriate, be carried out later in suitable compounds of the general formula (I).

In general, it is advantageous to carry out the preparation process 1 according to the invention in the presence of diluents, if appropriate, and in the presence of basic reaction auxiliaries, if appropriate.

Diluents are advantageously employed in such an amount that the reaction mixture remains readily stirable during the entire process. Suitable diluents for carrying out the process 1 according to the invention are all organic solvents which are inert under the reaction conditions.

Examples which may be mentioned are: halogenated hydrocarbons, in particular chlorinated hydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers, such as ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide; amines, such as trimethylamine, triethylamine, tripropylamine, tributyl amine, N-methylmorpholine, pyridine and tetramethylenediamine; nitrated hydrocarbons, such as nitromethane, nitroethane, nitropropane, nitrobenzene, chloronitrobenzene, o-nitrotoluene; nitriles, such as acetonitrile, propionitrile, butyronitrile, isobutyronitrile, benzonitrile, m-chlorobenzonitrile and also compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones, such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons, such as pentane, hexane, heptane, octane, nonane and industrial hydrocarbons, for example white spirits with components having boiling points in the range of, for example, from 40° C. to 250° C., cymene, petroleum fractions having a boiling point interval of from 70° C. to 190° C., cyclohexane, methylcyclohexane, petroleum ether, ligroin, octane, benzene, toluene, chlorobenzene, bromobenzene, nitrobenzene, xylene; esters, such as methyl acetate, ethyl acetate, butyl acetate, isobutyl acetate, and also dimethyl carbonate, dibutyl carbonate, ethylene carbonate; amides, such as hexamethylenephosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine; ketones, such as acetone, acetophenone, methyl ethyl ketone, methyl butyl ketone.

It is, of course, also possible to use mixtures of the solvents and diluents mentioned for the process according to the invention.

However, preferred diluents for carrying out the preparation process according to the invention are ethers, such as ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide; preference is given to tetrahydrofuran and dioxane and also to cycloaliphatic or aromatic hydrocarbons, such as pentane, hexane, heptane, octane, nonane and industrial hydrocarbons; for example white spirits with components having boiling points in the range of, for example, from 40° C. to 250° C.; preference is given to pentane and hexane.

Suitable basic reaction auxiliaries for carrying out the preparation process 1 according to the invention are all suitable acid binders, such as amines, in particular tertiary amines, and also alkali metal and alkaline earth metal compounds.

Examples which may be mentioned are the hydroxides, hydrides, oxides and carbonates of lithium, sodium, potassium, magnesium, calcium and barium, furthermore further basic compounds, such as amidine bases or guanidine bases, such as 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine, tertiary amines, such as triethylamine, trimethylamine, tribenzylamine, triisopropylamine, tributylamine, tricyclohexylamine, triamylamine, trihexylamine, N,N-dimethylaniline, N,N-dimethyltoluidene, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, β-picoline, isoquinoline, pyrimidine, acridine, N,N,N',N'tetramethylene-diamine, N,N,N'-tetraethylenediamine, quinoxaline, N-propyldiisopropylamine, N-ethyl-diisopropylamine, N,N'-dimethylcyclohexylamine, 2,6-lutidine, 2,4-lutidine or triethyldiamine.

Preference is given to using lithium diisopropylamide (LDA).

The reaction of compounds of the general formula (II) according to preparation process is carried out:
Route A: by halogenating the compounds of the general formula (II) in the presence of a basic reaction auxiliary, for example n-butyllithium, in one of the stated diluents and at −78° C., preferably with bromine.
Route B: by reacting the compounds of the general formula (II) in the presence of a basic reaction auxiliary, for example lithium diisopropylamide (LDA), in one of the stated diluents.

The reaction time is from 5 minutes to 48 hours. The reaction is carried out at temperatures between −100° C. and +200° C., preferably between −90° C. and 150° C., particularly preferably between −80° C. and 100° C.

In principle, the reaction can be carried out under atmospheric pressure. The reaction is preferably carried out at atmospheric pressure or at pressures of up to 15 bar and, if appropriate, under an atmosphere of protective gas (nitrogen, helium or argon).

For carrying out the preparation process 1 according to the invention, in general from 0.5 to 4.0 mol, preferably from 0.7 to 3.0 mol, particularly preferably from 1.0 to 2.0 mol, of basic reaction auxiliary (routes A and B) and halogen, in particular bromine (route A) are employed per mole of compound of the general formula (II).

After the reaction has gone to completion, the entire reaction mixture is concentrated. The products obtained after work-up can be purified in a customary manner by recrystallization, distillation under reduced pressure or column chromatography (cf. also the Preparation Examples).

Racemates or diastereomer mixtures can be separated by column chromatography, if appropriate on a suitable chiral phase, into the corresponding enantiomers or individual diastereomers. The absolute configuration can be determined with the aid of X-ray structure analysis after crystallization of the substance (cf. also the Preparation Examples).

If, in the preparation process 2 according to the invention for preparing the novel compounds of the general formula (I), the compound of the formula (III) used is, for example, 5-[2-(chloromethyl)prop-2-en-1-yl]-4-pyrrolidin-1-ylfuran-2 (5H)-one and the compound of the general formula (IV) is 3-aminomethyl-6-chloropyridine, this can be reacted in a first reaction step to give 5-[2-({[(6-chloropyridin-3-yl)methyl]amino}methyl)prop-2-en-1-yl]-4-pyrrolidin-1-ylfuran-2 (5H)-one as compound of the general formula (V) which is then subjected to an intramolecular cyclization in the second reaction step (reaction scheme VI):

Scheme VI

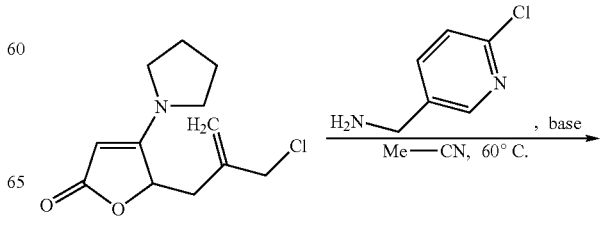

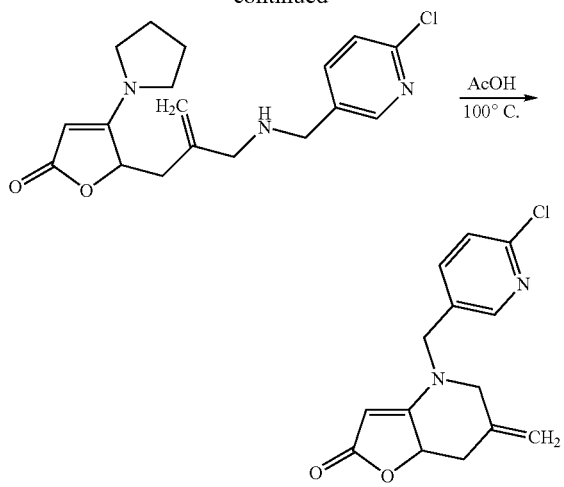

The formulae (III) and (IV) provide general definitions of the compounds required as starting materials for carrying out the preparation process 2 according to the invention.

In these formulae (III) and (IV), A, B, E, Z, LG, $R^1$, $R^2$, $R^4$, $D^1$, $D^2$, n, m, Q preferably represent those radicals which have already been mentioned in connection with the description of the compounds of the general formula (I) according to the invention as preferred substituents.

The formula (V) provides a general definition of the compounds to be used in particular for carrying out the second reaction step of preparation process 2 according to the invention.

The compounds of the general formula (V) can be obtained by methods known from the literature, for example by the reaction process shown in reaction scheme VII.

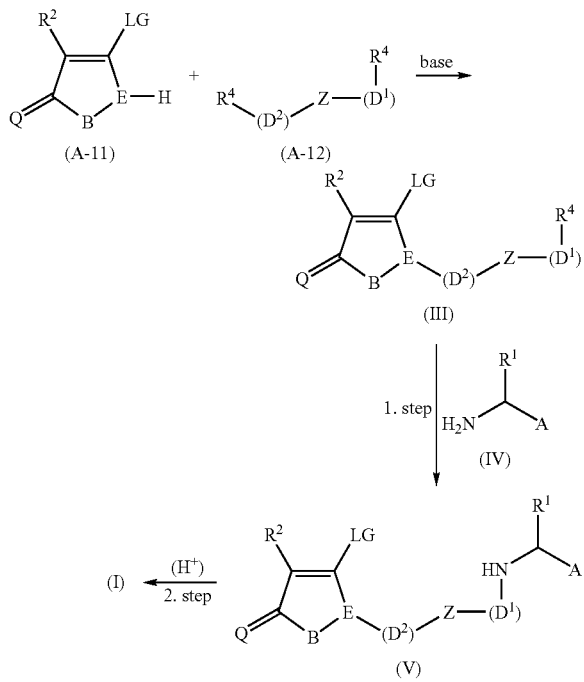

LG = leaving group, for example sec. amino group, hydroxyl, alkoxy, alkylthio

Suitable starting materials (A-11) for preparing the compounds of the general formula (III) are, for example, 4-aminofuran-2(5H)-ones (B, Q=oxygen, E-$R^3$=$CH_2$, LG=N-pyrrolidinyl, methoxy; cf. Shandala, M. Y. et al. J. Heterocycl. Chem. (1984), 21, 1753-1754; Momose T. et al. Heterocycles (1988), 27, 1907-1923).

In general, it is advantageous to carry out the conversion of compounds (A-11) and (A-12) into compounds of the general formula (III) in the presence of diluents, if appropriate, and in the presence of basic reaction auxiliaries, if appropriate.

Diluents are advantageously employed in such an amount that the reaction mixture remains readily stirable during the entire process. Suitable diluents for carrying out the process 2 according to the invention are all organic solvents which are inert under the reaction conditions.

Preferred diluents for carrying out the first reaction step of the preparation process according to the invention are ethers, such as ethyl propyl ether, methyl tert-butyl ether, n-butyl ether, dipropyl ether, diisopropyl ether, di-n-butyl ether, diisobutyl ether, diisoamyl ether, ethylene glycol dimethyl ether, tetrahydrofuran, dioxane, preferably tetrahydrofuran and dioxane, and also aliphatic hydrocarbons, such as pentane, hexane or heptane.

A preferred basic reaction auxiliary used for preparing the compounds of the general formula (III) is tert-butyllithium.

The reaction time is from 10 minutes to 48 hours. The reaction is carried out at temperatures between −100° C. and +140° C., preferably between −90° C. and 120° C., particularly preferably between −80° C. and 100° C. In principle, the reaction can be carried out under atmospheric pressure. The reaction is preferably carried out at atmospheric pressure or at pressures of up to 15 bar and, if appropriate, under an atmosphere of protective gas (nitrogen, helium or argon).

In general, it is advantageous to carry out the first reaction step of the preparation process 2 according to the invention in the presence of diluents, if appropriate, and in the presence of basic reaction auxiliaries, if appropriate.

Preferred diluents for carrying out the first reaction step of the preparation process according to the invention are nitriles, such as acetonitrile, propionitrile, butyronitrile, isobutyronitrile, benzonitrile, m-chlorobenzonitrile, particularly preferably acetonitrile.

It is, of course, also possible to use mixtures of the solvents and diluents mentioned for the first reaction step of the preparation process 2 according to the invention.

Preferred basic reaction auxiliaries for carrying out the first reaction step of the preparation process 2 according to the invention are tertiary amines, such as triethylamine, trimethylamine, tribenzylamine, triisopropylamine, tributylamine, tricyclohexylamine, triamylamine, trihexylamine, N-methylpyrrolidine or N-ethyl-N-isopropylpropane-2-amine, in particular N-ethyl-N-isopropylpropane-2-amine.

The reaction time is from 10 minutes to 48 hours. The reaction is carried out at temperatures between −100° C. and +140° C., preferably between −90° C. and 120° C., particularly preferably between −80° C. and 100° C. In principle, the reaction can be carried out under atmospheric pressure. The reaction is preferably carried out at atmospheric pressure or at pressures of up to 15 bar and, if appropriate, under an atmosphere of protective gas (nitrogen, helium or argon).

For carrying out the second reaction step of the preparation process 2 according to the invention, the compound is subjected to an intramolecular cyclization in the presence of an acidic reaction auxiliary, if appropriate in the presence of a diluent.

Here, suitable acidic reaction auxiliaries are virtually all mineral acids, organic acids or Lewis acids. The mineral acids preferably include hydrohalic acids, such as hydrofluoric acid, hydrochloric acid, hydrobromic acid or hydroiodic acid, and also sulphuric acid, phosphoric acid, phosphorus acid, nitric acid, and the Lewis acids preferably include aluminium (III) chloride, boron trifluoride or its etherate, titanium(V) chloride, tin(V) chloride. The organic acids include formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid.

The intramolecular cyclization is preferably carried out in the presence of an organic carboxylic acid, for example acetic acid.

After the reaction has gone to completion, the entire reaction mixture is concentrated. The products obtained after work-up can be purified in a customary manner by recrystallization, distillation under reduced pressure or column chromatography (cf. also the Preparation Examples).

The compounds of the general formula (Ia) in which $D^1$-Z-$D^2$ as a group represents —$CH_2$—C(=$CH_2$)—$CH_2$— (cf. for example, preparation process 2, scheme VI) can be converted, for example, by methods known from the literature (cf. reaction steps [A]-[F]) into compounds of the general formulae (Ib) to (Ig) in which $D^1$-Z-$D^2$ as a group represents —$CH_2$—CH($CH_3$)—$CH_2$— (Ib), —$CH_2$—COH($CH_2$—OH)—$CH_2$— (Ic), —$CH_2$—CO—$CH_2$— (Id), —$CH_2$—CH(OH)—$CH_2$— (Ie), —$CH_2$—C(Hal)$_2$-$CH_2$—(If) and —$CH_2$—CH(Hal)-$CH_2$— (Ig) (reaction scheme IX).

hydroxide, etc.), nickel catalysts, for example reduced nickel, nickel oxide, Raney-nickel etc.), ruthenium catalysts, cobalt catalysts (for example reduced cobalt, Raney-cobalt, etc.), copper catalysts (for example reduced copper, Raney-copper, Ullmann-copper, etc.). However, preference is given to using noble metal catalysts, such as, for example, platinum and palladium or ruthenium catalysts, if appropriate on a suitable support, such as, for example, on carbon or silicon, rhodium catalysts, such as, for example, tris(triphenylphosphine)rhodium(I) chloride in the presence of triphenylphosphine.

It is, of course, also possible to considerably increase the proportion of an isomer in the isomer mixture or even to suppress completely the formation of a further isomer by using a "chiral hydrogenation catalyst", for example with chiral diphosphine ligands, for example (2S,3S)-(−)-2,3-bis(diphenylphosphino)butane [(S,S)-Chiraphos] (N. K. Roberts in "Catalytic Aspects of Metal Phosphine Complexes", ACS Washington, p. 337 (1982)) or (R)-(+)-2,2'- or (S)-(−)-2,2'-bis(diphenylphosphino)-1,1'-binaphthalene [R(+)-BINAP and S(−)-BINAP, respectively] (cf. A. Miyashita et al. Tetrahedron 40, 1245 (1984)).

Preferred hydrogenation catalysts for reaction step [A] are rhodium catalysts, in particular a mixture of tris(triphenylphosphine)rhodium(I) chloride and triphenylphosphine.

Suitable for use as inert organic diluents are benzene or toluene.

With the aid of reaction steps [B] and [C], the compounds of the general formula (Ia) in which $D^1$-Z-$D^2$ as a group Scheme IX

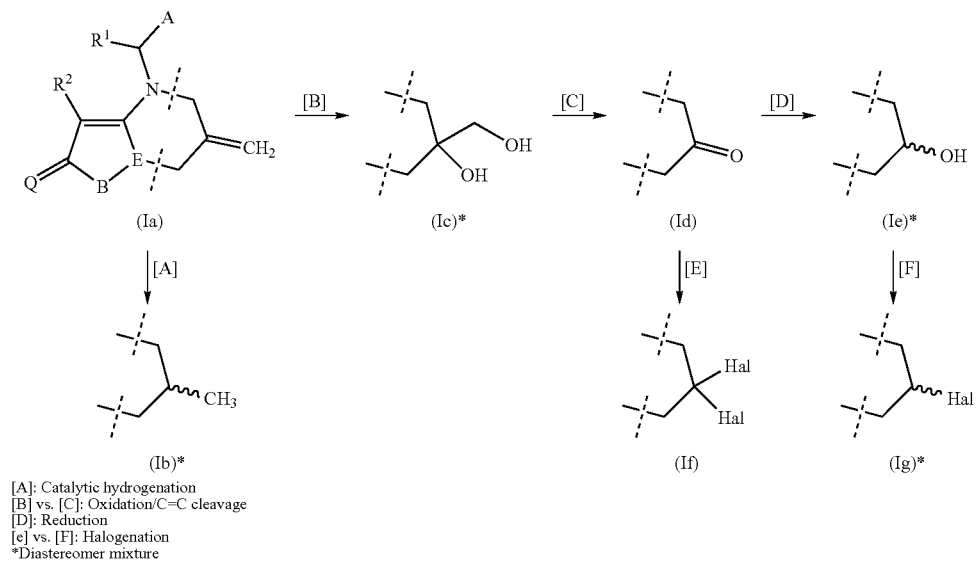

[A]: Catalytic hydrogenation
[B] vs. [C]: Oxidation/C=C cleavage
[D]: Reduction
[e] vs. [F]: Halogenation
*Diastereomer mixture In reaction step [A], the unsaturated compounds of the general formula (Ia) in which $D^1$-Z-$D^2$ as a group represents —$CH_2$—C(=$CH_2$)—$CH_2$— can be converted in the presence of suitable hydrogenation catalysts into saturated compounds of the formula (Ib) ($D^1$-Z-$D^2$=-$CH_2$—CH($CH_3$)—$CH_2$—). Suitable catalysts for carrying out the catalytic hydrogenation are all customary hydrogenation catalysts, such as, for example, platinum catalysts (platinum plate, platinum sponge, platinum black, colloidal platinum, platinum oxide, platinum wire, etc.), palladium catalysts (for example palladium sponge, palladium black, palladium oxide, palladium/carbon, colloidal palladium, palladium/barium sulphate, palladium/barium carbonate, palladium represents —$CH_2$—C(=$CH_2$)—$CH_2$— are converted in the presence of suitable oxidizing agents and compounds of the formula (Id) ($D^1$-Z-$D^2$=-$CH_2$—CO—$CH_2$—). Here, the compounds of the formula (Ic) ($D^1$-Z-$D^1$=-$CH_2$—COH($CH_2$—OH)—$CH_2$—) can be isolated as intermediates.

A large number of different oxidizing agents are known to be suitable for the oxidation/cleavage of a methylene grouping (cf. cleavage of (i) with formation of (iii) and (iv) according to reaction steps [B] and [C] in reaction scheme X) (cf., for example, oxidizing agents in: Comprehensive Organic Transformations; R. C. Larock, Wiley-VCH, 1999; the literature cited on pages 1213-1215; Methods for the Oxidation of Organic Compounds; A. H. Haines, Academic Press 1985;

chapter 3.4, page 117; Houbel-Weyl Methoden der Organischen Chemie, Vol. VII/2b Ketones part II, Georg Thieme Verlag Stuttgart, 1976, page 1287).

Scheme X

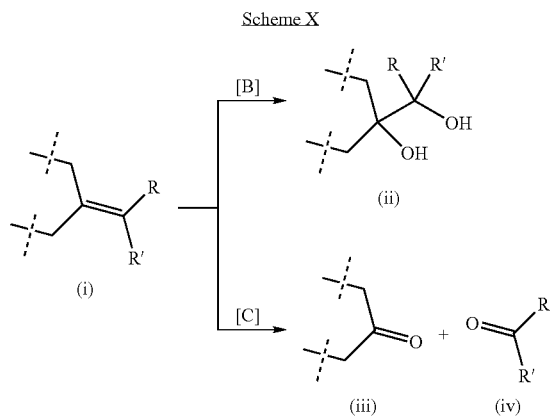

This can be followed by an oxidative cleavage (i.e. cleavage of (i) with formation of (iii) and (iv)), for example in the presence of ozone (cf. March's Advanced Organic Chemistry, Reactions, Mechanisms, and Structure, (Eds. M. B. Smith, J. March), 5th Edition, Wiley-Interscience Publication, John Wiley & Sons, Inc. 2001, page 1522 and page 1525) and with reaction mixtures in which ozone is used, such as, for example, in ozone/hydrogen with palladium/carbon, ozone/zinc or ozone/iodide and acetic acid, ozone dimethyl sulphide, ozone/thiourea, ozone/tri(n-butyl)phosphine [n-Bu$_3$P], ozone/triphenylphosphine, ozone/trimethyl phosphite [(MeO)$_3$P], ozone/pyridine, in the presence of permanganates, such as potassium permanganate, potassium permanganate and silica gel, in a mixture of potassium permanganate/aluminium/water, in the presence of periodates, such as sodium periodate and a catalytic amount of potassium permanganate, sodium periodate and a catalytic amount of ruthenium(III) chloride hydrate, sodium periodate and a catalytic amount of ruthenium dioxide, sodium periodate and a catalytic amount of osmium(VIII) oxide or sodium periodate and a catalytic amount of osmium(VIII) oxide/N-methylmorpholine.

The oxidation/cleavage of a methylene group may also proceed via a 1,2-diol structure (Ic; cf. ii) (cf. cleavage of (ii) with formation of (iii) and (iv)) in reaction scheme X). Numerous different oxidizing agents are known to be suitable for this purpose (cf., for example, March's Advanced Organic Chemistry, Reactions, Mechanisms, and Structure, (Eds. M. B. Smith, J. March), 5th Edition, Wiley-Interscience Publication, John Wiley & Sons, Inc. 2001, page 1519; Houbel-Weyl Methoden der Organischen Chemie, volume VI/1a Alcohols part I, Georg Thieme Verlag Stuttgart, 4. edition, 1979, page 592; Methods for the Oxidation of Organic Compounds; A. H. Haines, Academic Press 1985; chapter 3.2, page 73). The 1,2-diol structure may be cleaved, for example, even under mild reactions conditions in the presence of metal acetates, such as, for example, lead tetraacetate or periodic acid. Also known are acidic dichromates (cf. Chromium Oxidations in Organic Chemistry; Cainelli, Cardillo, Springer Verlag: New York, 1984; Reagents for Organic Synthesis; Fieser, Vol. 1, Wiley: New York, 1967, pp. 142-147, 1059-1064 and further volumes from this series) or permanganates, such as potassium permanganate, or periodates, such as, for example, sodium periodate. However, the oxidizing agents may also be attached to polymers (cf. Review: McKillop, Young Synthesis 401-422 (1979)). In this manner, both chromic acids and permanganates have been used as oxidizing agents. Also known are numerous phase-transfer reactions with permanganates, chromic acids (Tetrahedron Lett. 4167 (1977), Landini et al. 134 (1979)) and ruthenium tetroxide (Morris, Kiely J. Org. Chem. 52, 1149 (1987)). Even ultrasound-induced oxidation reactions are conceivable—thus, the use of potassium permanganate has been mentioned (Yamawaki et al. 379 (1983)).

The preferred oxidizing agent used for reaction step [B] is a mixture of osmium(VIII) oxide in tert-butanol and N-methylmorpholine N-oxide.

The inert organic solvents used are ethers, such as, for example, methyl tert-butyl ether, diisopropyl ether, tetrahydrofuran or dioxane, use is made, in particular, of tetrahydrofuran.

The preferred oxidizing agent used for reaction step [C] is sodium periodate.

The inert organic diluent used is a mixture of halogenated hydrocarbons, in particular chlorinated hydrocarbons, such as methylene chloride, and water in a ratio of (2:1).

In reaction step [D], the compounds of the general formula (Id) in which $D^1$-Z-$D^2$ as a group represents —$CH_2$—CO—$CH_2$— are converted in the presence of reducing agents suitable for carbonyl compounds in compounds of the formula (Ie) ($D^1$-Z-$D^2$=-$CH_2$—CH(OH)—$CH_2$—).

Reducing agents suitable for reducing a carbonyl group are various hydrogenating agents, such as, for example, alkali metal hydrides, in particular sodium borohydride (NaBH$_4$), lithium aluminium hydride (LiAlH$_4$), lithium triethylborohydride (Li[Et$_3$BH]), lithium tri-sec-borohydride (Li[sec-Bu$_3$BH], sodium bis(2-methoxyethoxy)aluminium hydride, alkylaluminium hydrides, in particular diisobutylaluminium hydride (DIBAL-H), or tetramethylammonium triacetoxyborohydride, inter alia (cf. H. de Koning, W. N. Houben-Weyl, Methoden der Organischen Chemie, Vol. E 21, Georg Thieme Verlag Stuttgart, p. 1953 and the literature cited therein). It is, of course, also possible to use a "borohydride resin", for example "Borohydride on Amberlite® IRA-406", for the hydrogenation (cf. A. R. Sande et al. Tetrahedron Lett. 25, 3501 (1984)).

Preferred reducing agents for reaction step [D] are alkali metal hydrides, in particular sodium borohydride.

Preferred for use as inert organic diluents are alcohols, such as methanol or ethanol.

With the aid of reaction steps [E] and [F], the compounds of the general formulae (Id) and (Ie) in which $D^1$-Z-$D^2$ as a group represents —$CH_2$—CO—$CH_2$— and —$CH_2$—CH(OH)—$CH_2$— are converted in the presence of suitable halogenating agents into compounds of the formula (If) ($D^1$-Z-$D^2$=-$CH_2$—C(Hal)$_2$-$CH_2$—) and into compounds of the formula (Ig) ($D^1$-Z-$D^2$=-$CH_2$—CH(Hal)-$CH_2$—).

Suitable halogenating agents for converting (deoxygenating) a carbonyl group or the 1,3-benzodioxole thereof (formed by a reaction of the carbonyl compound with 1,2-dihydroxybenzene) into a gem-halogenated methylene group are numerous halogenating agents, for example sulphur tetrafluoride (SF$_4$)/20% HF (cf. D. G. Martin, F. Kagan J. Org. Chem. 27, 3164 (1962)), carbonyl fluoride (COF$_2$) (F. S. Fawcett et al. J. Am. Chem. Soc. 84, 4275 (1962)), molybdenum hexafluoride (MoF$_6$) (F. Mathey, J. Bensoam Tetrahedron 27, 3965 (1971)) or N,N-diethylaminosulphur trifluoride (Et$_2$NSF$_3$, DAST) (K. A. Jolliffe Aust. J. Chem. 54, 75 (2001)) [for gem-difluoromethylene]; tungsten hexachloride (WCl$_6$) (M. F. Jung, J. I. Wasserman Tetrahedron Lett. 44, 7273 (2003)) [for gem-dichloromethylene]; 1,2-dihydroxybenzene/boron tribromide (via cleavage of the 1,3-benzodioxole) E. Napolitano et al. Synthesis 2, 122 (1986) [for gem-dibromomethylene]; 1,2-dihydroxybenzene/sodium iodide/acetyl chloride (via cleavage of the 1,3-benzodioxole) L. Corda et al. J. Het. Chem. 25, 311 (1988) [for gem-di-iodomethylene].

Suitable halogenating agents for converting a hydroxyl group into a halogen group are all halogenating agents suitable for this purpose, for example hydrofluoric acid (HF), sulphur tetrafluoride/hydrofluoric acid (HF) (J. Kollonitsch et al. J. Org. Chem. 44, 771 (1979)), N-(2-chloro-1,1,2-trifluoroethyl)diethylamine (cf. WO 2006103985 A1), N,N-diethylaminosulphur trifluoride ($Et_2NSF_3$, DAST) (K. A. Jolliffe Aust. J. Chem. 54, 75 (2001)), pyridinium poly(hydrogen fluoride) (30% pyridine-70% HF) (G. A. Olah et al. J. Org. Chem. 44, 3872 (1979)) [for mono-fluoromethylene]; phosgene ($COCl_2$), thionyl chloride, phosphorus oxychloride, phosphorus(III) chloride, phosphorus(V) chloride, a mixture of carbon tetrachloride ($CCl_4$) (cf., for example, Y. Berger et al., J. Med. Chem. 48, 483 (2005)) and triphenylphosphine [for mono-chloromethylene]; thionyl bromide, phosphorus (III) bromide, polymer-supported phosphorus(III) bromide ($PBr_3$ in Amberlite IRA 93) (G. Cainelli et al. Synthesis 4, 306 (1983)), a mixture of N-bromosuccinimide and triphenylphosphine (A. K. Bose, B. Lal Tetrahedron 40, 3937 (1973)), a mixture of carbon tetrabromide ($CBr_4$) and triphenylphosphine (cf., for example, S. Hanessian et al. Can. J. Chem. 65, 1859 (1987)) [for mono-bromomethylene]; diphosphorus tetraiodide ($P_2I_4$) (M. Lauwers et al. Tetrahedron Lett. 20, 1801 (1979)), a mixture of chlorotrimethylsilane and sodium iodide (T. Morita et al. Synthesis 5, 379 (1979)), a mixture of hexadimethylsilane and iodine (G. A. Olah et al. Angew. Chem. 91, 648 (1979)) [for mono-iodomethylene].

For reaction step [E], the halogenating agent used is in particular N,N-diethylaminosulphur trifluoride (DAST) (halogen: fluorine).

Suitable for use as inert organic diluents are halogenated hydrocarbons, in particular chlorinated hydrocarbons, such as methylene chloride.

For reaction step [F], the halogenating agents used are preferably mixtures of carbon tetrahalides (halogen: bromine, chlorine) and triphenylphosphine or DAST (halogen: fluorine).

Suitable for use as inert organic diluent are nitrites, such as, for example, acetonitrile, or halogenated hydrocarbons, in particular chlorinated hydrocarbons, such as methylene chloride (reaction with DAST).

The compounds of the general formulae (Ib), (Ic), (Ie) and (Ig) are present as mixtures of diastereomers from which the diastereomers may be obtained by column chromatography (cf. also the Preparation Examples).

The compounds of the general formulae (Ih) and (Ii) in which $D^1$-Z-$D^2$ as a group represents —$CH_2$—$CH_2$—CH= or —CH=CH—$CH_2$— can be obtained easily, for example, from compounds of the general formulae (Ij; in which E=CH) or (Ie) vs. (Ig) in which $D^1$-Z-$D^2$ as a group represents —$CH_2$—$CH_2$—CH(OH)— (Ij), —$CH_2$—C(OH)—$CH_2$— (Ie) or —$CH_2$—CH(Hal)-$CH_2$— (Ig; Hal, for example, chlorine) and are therefore also formed as byproducts (cf. reaction scheme XI and Preparation Examples).

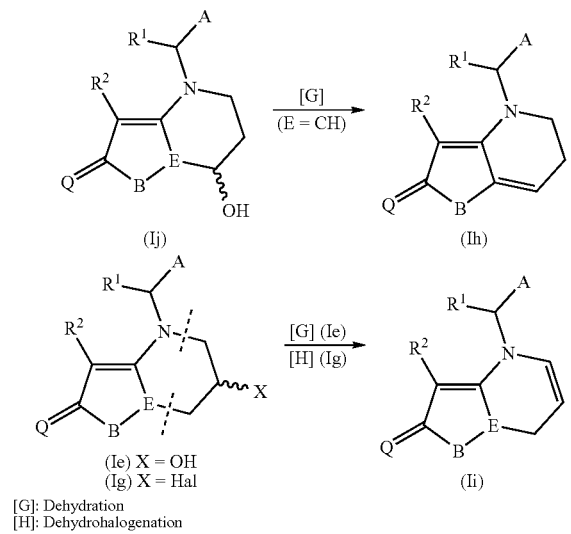

[G]: Dehydration
[H]: Dehydrohalogenation

Compounds of the general formulae (Ih) and (Ii) can be formed from compounds of the general formulae (Ij) and (Ie), for example by dehydration [reaction step G: acidic reaction auxiliary (for example trifluoroacetic acid)] or from compounds of the general formula (Ig) by dehydrohalogenation [reaction step H: triphenylphosphine, but also in the presence of basic reaction auxiliaries].

The compounds of the general formula (Ik in which, for example, $R^2$=H, B, Q=O, E=CH) in which $D^1$-Z-$D^2$ as a group represents —CO—$CH_2$— are accessible, for example, from compounds of the general formulae (XIa) and (XI) (cf. reaction scheme XII and Preparation Examples).

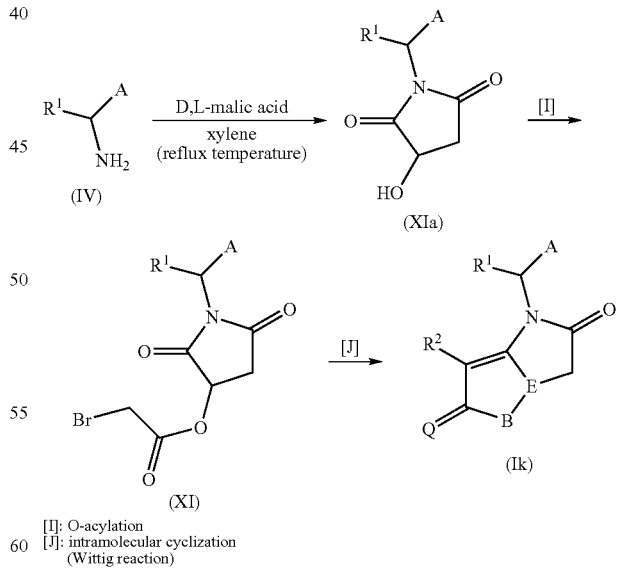

[I]: O-acylation
[J]: intramolecular cyclization (Wittig reaction)

The compounds of the general formula (XIa) can be prepared, for example, from compounds of the general formula (IV) and D,L-malic acid. The O-acylation [reaction step 1: basic reaction auxiliary (for example pyridine), bromacetyl bromide, diluent (for example dichloromethane); cf. Lee Y. S.

et al. Tetrahedron (1999), 55, 4631-4636] with formation of compounds of the general formula (XI) and their intramolecular cyclization to 4-substituted 6,6a-dihydro-2H-furo[3,2-b]pyrrole-2,5(4H)-dione systems of the general formula (Ik) is possible analogously to methods known from the literature [intramolecular Wittig reaction, step J: basic reaction auxiliary (for example triethylamine), triphenylphosphine, diluent (for example acetonitrile); $R^1$, $R^2$=H, B, Q=O; E=CH and A=COOEt: cf Niwa H et al. J. Org. Chem. (1987) 52, 2941-2943; analogously for A=-$CH_2CH_2$—CH=$CH_2$: cf. Lee Y. S. et al. Tetrahedron (1999), 55, 4631-4636; for A=6-chloropyrid-3-yl: cf. also Preparation Examples].

If in the preparation process 3 according to the invention for preparing the novel compounds of the general formula (I), in a first reaction step, the compound of the formula (VI) used is, for example, 4-{allyl-[(6-chloropyridin-3-yl)methyl]amino}furan-2(5H)-one, the preparation process 3 can be represented by reaction scheme XIII below:

Scheme XIII

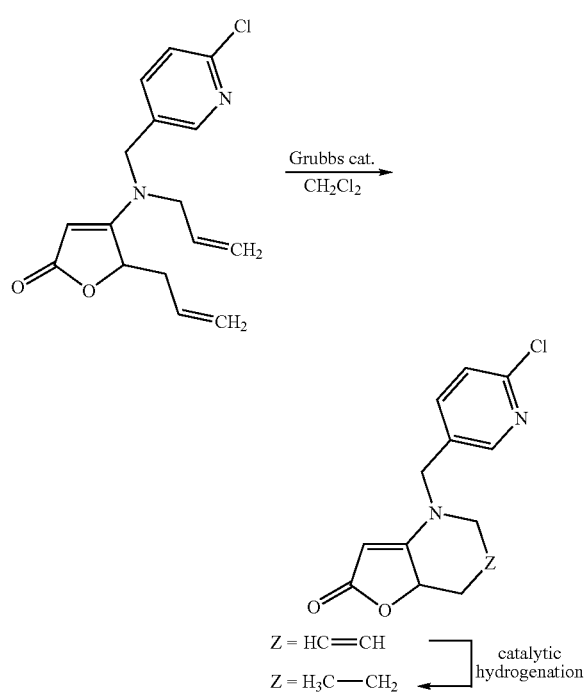

The formula (VI) provides a general definition of the compounds to be used as starting materials in particular for carrying out the preparation process 3 according to the invention.

In formula (VI), A, B, E, Z', $R^1$, $R^2$, $D^1$, $D^2$, n, m, Q are as defined further above for formula (I).

The compounds of the general formula (VI) can be obtained by methods known from the literature, for example by the preparation process shown in reaction scheme XIV.

Scheme XIV

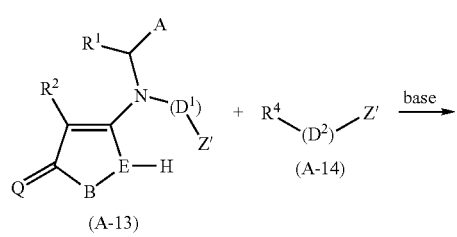

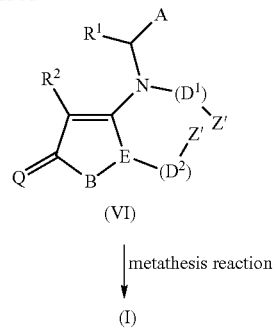

Suitable starting materials for preparing the compounds (A-13) are the compounds (A-1) mentioned farther above in scheme II. Further suitable starting materials for preparing the compounds (A-13) are secondary amines ($R^1$—CH(A)-NH-($D^1$)-Z'; $D^1$=optionally substituted carbon) in which Z' represents a C=C double bond or a C≡C triple bond.

The reaction of the compounds (A-13) with unsaturated compounds (A-14) is carried out according to the preparation process mentioned further above in reaction scheme VII, with formation of the precursors (VI) suitable for the subsequent metathesis reaction.

The metathesis reaction is known from the literature and can be carried out according to the reaction conditions known for this purpose, using known catalysts (cf, for example: Van de Weghe P. et al., Current Topics Med. Chem. (2005), 5, 1461-72. Deiters, A. et al., Chem. Rev. (Washington, D.C., United States) (2004), 104, 2199-2238. Nakamura, I.; Yamamoto, Y. Chem. Rev. (Washington, D.C., United States) (2004), 104, 2127-2198).

Here, by way of example and by way of preference, use is made of ruthenium catalysts which are also known as Grubbs catalysts of the first and second generation (for example Schmidt, B. Angew. Chem., Intern. Edition (2003), 42, 4996-4999).

In general, it is advantageous to carry out the preparation process 3 according to the invention in the presence of diluents. Diluents are advantageously employed in such an amount that the reaction mixture remains readily stirable during the entire process. Suitable diluents for carrying out the process 3 according to the invention are all organic solvents which are inert under the reaction conditions.

Preferred diluents for carrying out the process 3 according to the invention are, according to the process 1 mentioned further above, halogenated hydrocarbons, in particular chlorinated hydrocarbons, such as tetraethylene, tetrachloroethane, dichloropropane, methylene chloride, dichlorobutane, chloroform, carbon tetrachloride, trichloroethane, trichloroethylene or pentachloroethane; preference is given to using methylene chloride.

The reaction of compounds of the general formula (IV) according to preparation process 3 is carried out by reacting the compounds of the general formula (IV) in the presence of suitable catalysts, for example Grubbs catalysts of the second generation.

The reaction time is from 10 minutes to 48 hours. The reaction is carried out at temperatures between −10° C. and +200° C., preferably between +10° C. and 180° C., particularly preferably between 20° C. and 140° C. Very particularly preferably, the reaction is carried out at room temperature.

After the reaction has gone to completion, the entire reaction mixture is concentrated. The products obtained after work-up can be purified in a customary manner by recrystallization, distillation under reduced pressure or column chromatography (cf. also the Preparation Examples).

In a subsequent reaction step, the unsaturated compounds of the general formula (I) ($D^1$-Z-$D^2$=$H_2C$=HC=CH—$CH_2$) can be converted in the presence of suitable hydrogenation catalysts into saturated compounds of the formula (I) (Z=$H_2C$—$CH_2CH_2$—$CH_2$) (cf. scheme XII).

For the hydrogenation of compounds of the general formula (I), use is made of hydrogenation catalysts, preferably rhodium catalysts, in particular a mixture of tris(triphenylphosphine)rhodium(I) chloride and triphenylphosphine.

Suitable inert organic diluents are the diluents mentioned for process 1, such as, for example, benzene or toluene.

If, in the process 4 according to the invention for preparing the novel compounds of the general formula (I), in a first step the compound of the formula (VII) used is, for example, 3-chloro-5-hydroxymethyl-4-{[(6-chloropyridin-3-yl)methyl]amino}furan-2(5H)-one and the compound of the formula (VIII) or (IX) is formaldehyde or paraformaldehyde, the preparation process 4 can be represented by reaction scheme XV below:

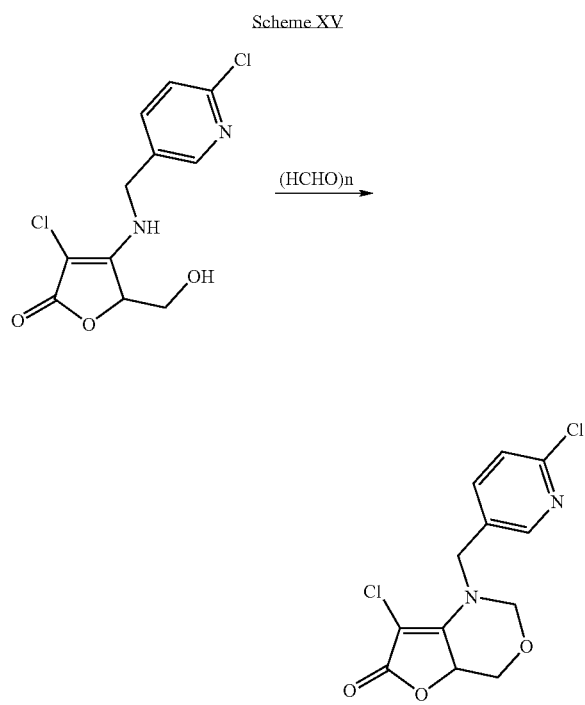

Scheme XV

The formula (VII) provides a general definition of the compounds to be used as starting materials in particular for carrying out the preparation process 4 according to the invention.

In the formula (VII), A, B, E, Z, $R^1$, $R^2$, $D^2$, Q are as defined further above for formula (I).

The compounds of the general formula (VII) can be obtained by methods known from the literature (for example EP 0539588 A1) or according to process 1, mentioned further above. The starting material 4-hydroxyfuran-2(5H)-one, used in process 4, can be obtained, for example, from 5-benzyloxymethyl-4-hydroxyfuran-2(5H)-one, which is known from the literature (Aragon, D. T. et al., J. Org. Chem. 68, 3363-3365, 2003), by debenzylation. Subsequent reaction with 3-aminomethyl-6-chloropyridine and halogenation by a method mentioned further below using, for example, N-chlorosuccinimide then affords 3-chloro-5-hydroxymethyl-4-{[(6-chloropyridin-3-yl)methyl]amino}furan-2(5H)-one (cf. also Preparation Examples).

In the formula (VIII) or (IX), R' is as defined further above for formula (I).

The compounds of the formulae (VIII) and (IX) are generally known and commercially available.

In general, it is advantageous to carry out the preparation process 4 according to the invention in the presence of diluents and in the presence of an acidic reaction auxiliary.

Suitable diluents for carrying out the preparation process 4 according to the invention are all organic solvents inert under the reaction conditions which are mentioned further above under process 1.

Preferred diluents for carrying out the preparation process 4 according to the invention are, corresponding to the preparation process 1 mentioned further above, aromatic hydrocarbons, such as benzene, toluene, chlorobenzene, bromobenzene, nitrobenzene or xylene, and in particular benzene and toluene. To improve the solubility, if appropriate, it may also be possible to add small amounts of amides, such as N,N-dimethylformamide, N,N-dipropylformamide, N,N-dibutylformamide or N-methylpyrrolidine, in particular N,N-dimethylformamide.

Preferred acidic reaction auxiliaries are organic acids, such as acetic acid, benzenesulphonic acid or para-toluenesulphonic acid, in particular para-toluenesulphonic acid.

The reaction of compounds of the general formula (VII) according to preparation process 4 is carried out by reacting the compounds of the general formula (VII) with compounds of the general formula (VIII) or (IX) in the presence of an acidic reaction auxiliary in one of the diluents stated.

The reaction time is from 10 minutes to 48 hours. The reaction is carried out at temperatures between −10° C. and +200° C., preferably between +10° C. and 180° C., particularly preferably between 60° C. and 140° C. The reaction is preferably carried out under reaction conditions which allow water to be separated off or to be removed, for example with the aid of a water separator.

After the reaction has gone to completion, the entire reaction mixture is concentrated. The products obtained after work-up can be purified in a customary manner by recrystallization, distillation under reduced pressure or column chromatography (cf. also the Preparation Examples).

To prepare compounds of the general formula (I) in which $R^2$ is halogen, it is alternatively and according to the invention also possible to react compounds of the general formula (I) in which $R^2$ represents hydrogen in the presence of basic reaction auxiliaries with halogenating agents, according to reaction step [K] in reaction scheme (XVI).

Scheme XVI

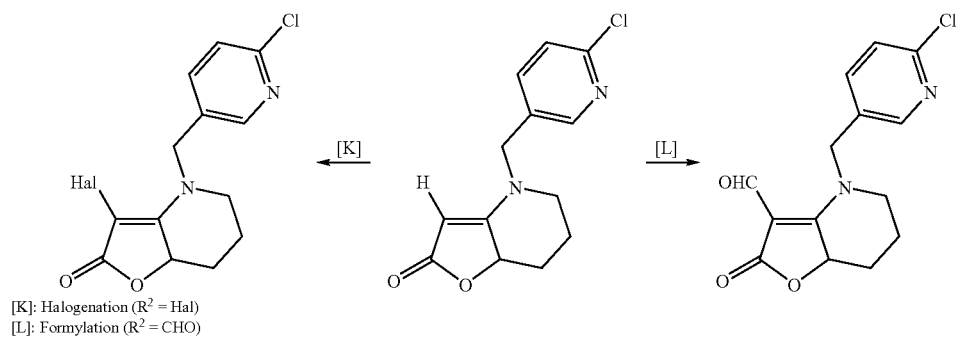

[K]: Halogenation ($R^2$ = Hal)
[L]: Formylation ($R^2$ = CHO)

In the compounds of the formula (I) required as starting materials for a halogenation, A, B, E, Z, Q, $D^1$, $D^2$, $R^1$ and $R^2$ are as defined further above, the substituent $R^2$ represents hydrogen.

The compounds of the general formula (I) can be obtained by the preparation processes 1 to 4 mentioned above.

In general, it is advantageous to carry out the halogenation in the presence of diluents. Diluents are advantageously employed in such an amount that the reaction mixture remains readily stirable during the entire process. Suitable diluents for carrying out the halogenation are all organic solvents which are inert under the reaction conditions.

Suitable for use as halogenating agents for carrying out the process according to the invention are all suitable halogenating agents, such as N-halo compounds.

Examples which may be mentioned are N-haloamines, such as 1-chloromethyl-4-fluorodiazoniabicyclo[2.2.2]octane-bis-(tetrafluoroborate) (Selectfluor®), N,N-dihaloamines, N-halocarboxamides, N-halocarbamic acid esters, N-halourea, N-halosulphonylamides, N-halodisulphonylamides, N-halosulphonylimides, such as N-fluorobis[(trifluoromethyl)-sulphonyl]imide, and N-halocarboxylic acid diamides, such as N-chlorophthalimide, N-bromophthalimide, N-iodophthalimide, N-chlorosuccinimide (NCS), N-bromosuccinimide (NBS), N-bromosaccharin or N-iodosuccinimide.

Preferred halogenating agents for carrying out the halogenation are the N-halocarboxylic acid diamides (Hal=bromine, chlorine or iodine) or 1-chloromethyl-4-fluoro-diazoniabicyclo[2.2.2]octane-bis-(tetrafluoroborate) (Selectfluor®; cf. also P. T. Nyffeler et al. Angew. Chem. (2004), 116, 2-23) (Hal=fluorine).

Preferred diluents for carrying out the halogenation are, corresponding to the process 2 mentioned further above, nitriles, such as acetonitrile, propionitrile, butyronitrile, isobutyronitrile, benzonitrile, m-chlorobenzonitrile.

It is, of course, also possible to use mixtures of the solvents and diluents mentioned for the process according to the invention.

However, preferred diluents for carrying out the preparation process according to the invention are nitriles, such as acetonitrile, propionitrile or butyronitrile.

The halogenation of compounds of the general formula (I) is carried out by reacting these in the presence of basic reaction auxiliaries with suitable halogenating agents.

The reaction time is from 10 minutes to 48 hours. The reaction is carried out at temperatures between −10° C. and +100° C., preferably between 0° C. and 60° C., particularly preferably between 10° C. and room temperature.

After the reaction has gone to completion, the entire reaction mixture is concentrated. The products obtained after work-up can be purified in a customary manner by recrystallization, distillation under reduced pressure or column chromatography (cf. also the Preparation Examples).

To prepare the compounds of the general formula (I) in which $R^2$ represents formyl, it is alternatively and according to the invention also possible to react compounds of the general formula (I) in which $R^2$ represents hydrogen according to suitable methods allowing, according to reaction step [L], the introduction of the formyl group (cf. reaction scheme XVI and Preparation Examples).

A suitable method for introducing the formyl group is, for example, the Vilsmeier reaction (cf. Houben-Weyl, Methoden der Organischen Chemie, vol. VII/1, Georg Thieme Verlag Stuttgart, p. 30; L. N. Ferguson Chem. Rev. (1946), 38, 230). Here, it is possible to use N-methylformanilide, N-methyl- or N,N-dimethylformamide and phosphoryl chloride or alternatively N,N-dimethylthioformamide and phthalic anhydride.

In reaction step [L], for introducing the formyl group in the absence of an inert organic diluent, preference is given to using a mixture of N,N-dimethylformamide and phosphoryl chloride (cf. also the Preparation Examples).

To prepare the compounds of the general formula (I) in which E represents CH-alkyl, it is alternatively and according to the invention also possible to react compounds of the general formula (I) in which E represents CH in the presence of basic auxiliaries with suitable alkylating agents, according to reaction scheme (XVII).

Scheme XVII

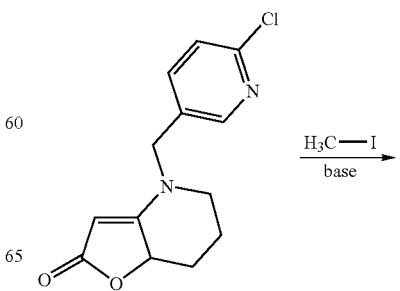

-continued

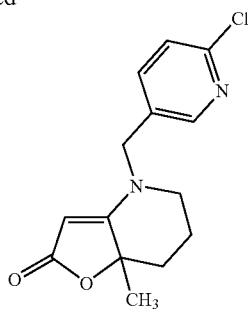

In the compounds of the formula (I) required as starting materials for carrying out the C-alkylation, A, B, E, Z, Q, $D^1$, $D^2$, $R^1$ and $R^2$ are as defined further above, the substituent $R^2$ represents hydrogen.

The compounds of the general formula (I) can be obtained by the preparation processes 1 to 4 mentioned above.

In general, it is advantageous to carry out the C-alkylation in the presence of diluents. Diluents are advantageously employed in such an amount that the reaction mixture remains readily stirable during the entire process. Suitable diluents for carrying out the C-alkylation are all organic solvents which are inert under the reaction conditions.

Preferred diluents for carrying out the C-alkylation are ethers, such as methyl tert-butyl ether, butylether, n-butyl ether, anisole, phenetol, cyclohexyl methyl ether, diisopropyl ether, diisobutyl ether, diisoamyl ether, ethylene glycol dimethyl ether, tetrahydrofuran, dioxane, dichlorodiethyl ether and polyethers of ethylene oxide and/or propylene oxide.

It is, of course, also possible to use mixtures of the solvents and diluents mentioned for the process according to the invention.

However, preferred diluents for carrying out the process according to the invention are ethers, such as methyl tert-butyl ether, or cyclic ethers, such as tetrahydrofuran and dioxane.

The C-alkylation of compounds of the formula (I) is carried out by reaction with suitable alkylating agents in the presence of basic reaction auxiliaries.

The reaction time is from 10 minutes to 48 hours. The reaction is carried out at temperatures between −100° C. and +20° C., preferably between −90° C. and 10° C., particularly preferably between −80° C. and 0° C.

After the reaction has gone to completion, the entire reaction mixture is concentrated. The products obtained after work-up can be purified in a customary manner by recrystallization, distillation under reduced pressure or column chromatography (cf also the Preparation Examples).

If appropriate, the compounds of the formula (I) can be present in different polymorphic forms or as a mixture of different polymorphic forms. Both the pure polymorphs and the polymorph mixtures are provided by the invention and can be used according to the invention.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp. From the order of the Chilopoda, for example, *Geophilus* spp., *Scutigera* spp. From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Stemechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp.,

*Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control protozoa, such as Eimeria.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Cameocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis elysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella gernanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable Solid Carriers are: for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or —POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

Particularly favourable mixing components are, for example, the following compounds:
Fungicides:
Inhibitors of Nucleic Acid Synthesis
  benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid
Inhibitors of Mitosis and Cell Division
  benomyl, carbendazim, diethofencarb, fuberidazole, pencycuron, thiabendazole, thiophanatmethyl, zoxamide
Inhibitors of Respiratory Chain Complex I
  diflumetorim
Inhibitors of Respiratory Chain Complex II
  boscalid, carboxin, fenfuram, flutolanil, furametpyr, mepronil, oxycarboxin, penthiopyrad, thifluzamide
Inhibitors of Respiratory Chain Complex III
  azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin
Decouplers
  dinocap, fluazinam
Inhibitors of ATP Production
  fentin acetate, fentin chloride, fentin hydroxide, silthiofam
Inhibitors of Amino Acid Biosynthesis and Protein Biosynthesis
  andoprim, blasticidin-S, cyprodinil, kasugamycin, kasugamycin hydrochloride hydrate, mepanipyrim, pyrimethanil
Inhibitors of Signal Transduction
  fenpiclonil, fludioxonil, quinoxyfen
Inhibitors of Lipid and Membrane Synthesis
  chlozolinate, iprodione, procymidone, vinclozolin
  ampropylfos, potassium-ampropylfos, edifenphos, iprobenfos (IBP), isoprothiolane, pyrazophos
  tolclofos-methyl, biphenyl
  iodocarb, propamocarb, propamocarb hydrochloride
Inhibitors of Ergosterol Biosynthesis
  fenhexamid,
  azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipeonazole, metconazole, myclobutanil, paclobutrazole, penconazole, propiconazole, prothioconazole, simeconazole, tebuconazole, tetraconazole, triadimefon, triadimenol, triticonazole, uniconazole, voiiconazole, imazalil, imazalil sulphate, oxpoconazole, fenarimol, flurprimidole, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine Inhibitors of Cell Wall Synthesis benthiavalicarb, bialaphos, dimethomorph, flumorph, iprovalicarb, polyoxins, polyoxorim, validamycin A Inhibitors of Melanin Biosynthesis capropamid, diclocymet, fenoxanil, phthalid, pyroquilon, tricyclazole Resistance Inductors acibenzolar-S-methyl, probenazole, tiadinil Multisite captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram Unknown Mechanism amibromdol, benthiazol, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulphate, diphenylamine, ethaboxam, ferimzone, flumetover, flusulphamide, fluopicolide, fluoroimide, hexachlorobenzene, 8-hydroxy-quinoline sulphate, irumamycin, methasulfocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrol nitrin, quintozene, tecloftalam, tecnazene, triazoxide, trichlamide, zarilamide and 2,3,5,6-tetrachloro-4-(methylsulphonyl)pyridine, N-(4-chloro-2-nitrophenyl)-N-ethyl-4-methylbenzenesulphonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxy-phenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulphon-yl)amino]butanamide, 5-chloro-7-(4-methylpiperidin-1-yl)-6-(2,4,6-trifluorophenyl)[1,2,4]-triazolo[1,5-a]pyrimidine, 5-chloro-6-(2,4,6-trifluorophenyl)-N-[(1R)-1,2,2-trimethylpropyl]-[1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloro-nicotinamide, 2-butoxy-6-iodo-3-propylbenzopyranon-4-one, N-{(Z)-[(cyclopropylmethoxy)-imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoro-methyl)benzamide, N-(3',4'-dichloro-5-fluorobiphenyl-2-yl)-3-(difluoromethyl)-methyl-1H-pyrazole-4-carboxamide, N-(6-methoxy-3-pyridinyl)cyclopropanecarboxamide, 1-[(4-methoxyphenoxy)methyl]-2,2-dimethylpropyl]-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methyl-acetamide Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

Acetylcholine Esterase (AChE) Inhibitors carbamates, for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate organophosphates, for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers pyrethroids, for example acrinathrin, allethrin (d-cis-trans, d-trans), beta-cyfluthrin, bifenthrin, bioallethrin, bioallethrin-S- cyclopentyl isomer, bioethanomethrin, biopemmethrin, bioresmethrin, chlovaporthrin, cis-cypernethrin, cis-resmethrin, cis-pernethrin, clocythrin, cyloprothrin, cyfluthrin, cyhalothrin, cypennethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum)

DDT oxadiazines,
  for example indoxacarb
semicarbazones,
  for example metaflumizone (BAS3201)

Acetylcholine Receptor Agonists/Antagonists
  chloronicotinyls,
    for example acetamiprid, clothianidin, dinotefuran, imidacloprid, nitenpyram, nithiazine, thiacloprid, imidaclothiz, AKD-1022, thiamethoxam
  nicotine, bensultap, cartap Acetylcholine Receptor Modulators
  spinosyns,
    for example spinosad, spinetoram (XDE-175)

GABA-Controlled Chloride Channel Antagonists
  organochlorines,
    for example camphechlor, chlordane, endosulphan, gamma-HCH, HCH, heptachlor, lindane, methoxychlor
  fiprols,
    for example acetoprole, ethiprole, fipronil, pyrafluprole, pyriprole, vaniliprole Chloride Channel Activators
  mectins,
    for example abamectin, emamectin, emamectin-benzoate, ivermectin, lepimectin, milbemycin Juvenile Hormone Mimetics,
  for example diofenolan, epofenonane, fenoxycarb, hydroprene, kinoprene, methoprene, pyriproxifen, triprene Ecdysone Agonists/Disruptors
  diacylhydrazines,
    for example chromafenozide, halofenozide, methoxyfenozide, tebufenozide Chitin Biosynthesis Inhibitors
  benzoylureas,
    for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
  buprofezin
  cyromazine Oxidative Phosphorylation Inhibitors, ATP Disruptors
  diafenthiuron
  organotin compounds,
    for example azocyclotin, cyhexatin, fenbutatin-oxide Oxidative Phosphorylation Decouplers Acting by Interrupting the H-Proton Gradient
  pyrroles,
    for example chlorfenapyr
  dinitrophenols,
    for example binapacryl, dinobuton, dinocap, DNOC Site-I Electron Transport Inhibitors
  METIs,
    for example fenazaquin, fenpyroximate, pyrimidifen, pyridaben, tebufenpyrad, tolfenpyrad
  hydramethylnon
  dicofol Site-II Electron Transport Inhibitors
  rotenone Site-III Electron Transport Inhibitors
  acequinocyl, fluacrypyrim Microbial Disruptors of the Insect Gut Membrane
  *Bacillus thuringiensis* strains Lipid Synthesis Inhibitors
  tetronic acids,
    for example spirodiclofen, spiromesifen
  tetramic acids,
    for example spirotetramat
  carboxamides,
    for example flonicamid
  octopaminergic agonists,
    for example amitraz Inhibitors of Magnesium-Stimulated ATPase,
  propargite
  nereistoxin analogues,
    for example thiocyclam hydrogen oxalate, thiosultap-sodium Ryanodin Receptor Agonists
  benzoic acid dicarboxamides,
    for example flubendiamid
  anthronilamides,
    for example rynaxypyr (3-bromo-N-{4-chloro-2-methyl-6-[(methylamino)carbonyl]phenyl}-1-(3-chloropyridin-2-yl)-1H-pyrazole-5-carboxamide)

Biologicals, Hormones or Pheromones
  azadirachtin, *Bacillus* spec., *Beauveria* spec., codlemone, *Metarrhizium* spec., *Paecilomyces* spec., thuringiensin, *Verticillium* spec.

Active Compounds with Unknown or Unspecific Mechanisms of Action
  fumigants,
    for example aluminium phosphide, methyl bromide, sulphuryl fluoride
  antifeedants,
    for example cryolite, flonicamid, pymetrozine
  mite growth inhibitors,
    for example clofentezine, etoxazole, hexythiazox
  amidoflumet, benclothiaz, benzoximate, bifenazate, bromopropylate, buprofezin, chinomethionat, chlordimeform, chlorobenzilate, chloropicrin, clothiazoben, cyclopren, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulphluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds combinations is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

Treatment according to the invention of the plants and plant parts with the active compound combinations is carried out directly or by allowing the compounds to act on the surroundings, habitat or storage space by the customary treatment methods, for example by immersion, spraying, evaporation, fogging, scattering, painting on and, in the case of propagation material, in particular in the case of seeds, also by applying one or more coats.

The mixtures according to the invention are particularly suitable for treating seed. Here, the combinations according to the invention mentioned above as preferred or particularly preferred may be mentioned as being preferred. Thus, a large part of the damage to crop plants which is caused by pests occurs as early as when the seed is attacked during storage and after the seed is introduced into the soil, during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seeds of plants has been known for a long time and is subject-matter of continuous improvements. However, the treatment of seed frequently entails a series of problems which cannot always be solved in a satisfactory manner. Thus, it is desirable to develop methods for protecting the seed and the germinating plant which dispense with the additional application of crop protection agents after sowing or after the emergence of the plants. It is furthermore desirable to optimize the amount of active compound employed in such a way as to provide maximum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection agents being employed.

The present invention therefore in particular also relates to a method for the protection of seed and germinating plants from attack by pests, by treating the seed with a composition according to the invention. The invention likewise relates to the use of the compositions according to the invention for the treatment of seed for protecting the seed and the germinating plant from pests. Furthermore, the invention relates to seed which has been treated with a composition according to the invention so as to afford protection from pests.

One of the advantages of the present invention is that the particular systemic properties of the compositions according to the invention mean that treatment of the seed with these compositions not only protects the seed itself, but also the resulting plants after emergence, from pests. In this manner, the immediate treatment of the crop at the time of sowing or shortly thereafter can be dispensed with.

A further advantage is the synergistically increased insecticidal activity of the compositions according to the invention in comparison with the insecticidal individual active compound, which exceeds the total of the activity of the two active compounds when applied individually. Also advantageous is the synergistically increased fungicidal activity of the compositions according to the invention in comparison with the respective individual active compound, which exceeds the total of the activity of the active compound when applied individually. This makes possible an optimization of the amount of active compound employed.

Furthermore, it must be considered as advantageous that the mixtures according to the invention can also be employed in particular in transgenic seed, the plants arising from this seed being capable of expressing a protein directed against pests. By treating such seed with the compositions according to the invention, certain pests can be controlled merely by the expression of the, for example, insecticidal protein, and additionally be protected by the compositions according to the invention against damage.

The compositions according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, sorghum and millet, wheat, barley, oats, rye, sunflower, tobacco, potatoes or vegetables (for example tomatoes, cabbage plants). The compositions according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with a composition according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus*, *Rhizobium*, *Pseudomonas*, *Serratia*, *Trichoderma*, *Clavibacter*, *Glomus* or *Gliocladium*.

The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), system, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela gennanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dennacentor* spp., *Haemophysalis* spp., *Hyalomma* spp., *Rhipicephalus* spp., *Dermanyssus* spp., *Raillietia* spp., *Pneumonyssus* spp., *Stemostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zooternopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, such as hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Avicularidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalis, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

PREPARATION EXAMPLES

Method 1

Example I-1

1-[(6-Chloropyridin-3-yl)methyl]-2,3-dihydro-1H-furo[2,3-b][1,4]oxazin-6(4aH)-one

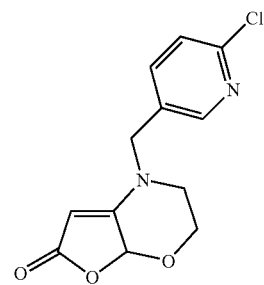

At −78° C., a solution of 202 mg (0.75 mmol) of 4-[[(6-chloropyridin-3-yl)methyl](2-hydroxyethyl)-amino]furan-2 (5H)-one (II-1) in 7 ml of tetrahydrofuran, also cooled to −78° C., is added to a mixture of 0.6 ml (1.50 mmol) of a 2.5M solution of n-butyllithium in hexane and 3 ml of tetrahydrofuran. After 20 minutes of stirring at −78° C., 39 µl (0.75 mmol) of bromine are added a little at a time, and stirring at −78° C. is continued for a further 30 min. After addition of saturated aqueous ammonium chloride solution, the mixture is warmed to room temperature and extracted with ethyl acetate. The combined organic phase is dried over magnesium sulphate and concentrated under reduced pressure. Purification of the residue by column chromatography on silica gel (silica gel 60, Merck, particle size: 0.04 to 0.063 mm) using the mobile phase mixture dichloromethane:methanol (95:5) gives 67 mg (32% of theory) of 1-[(6-chloropyridin-3-yl)methyl]-2,3-dihydro-1H-furo[2,3-b][1,4]oxazin-6 (4aH)-one.

$^1$H-NMR (CDCl$_3$): δ [ppm]=3.16 (m, 1 H), 3.26 (m, 1 H), 4.10 (m, 2 H), 4.19 (d, 1 H), 4.40 (d, 1 H), 4.88 (s, 1 H), 5.72 (s, 1 H), 7.38 (d, 1 H), 7.61 (dd, 1 H), 8.35 (d, 1 H).

Example I-2

4-[(6-Chloropyridin-3-yl)methyl]-5,6,7,7a-tetrahydrofuro[3,2-b]pyridin-2(4H)-one

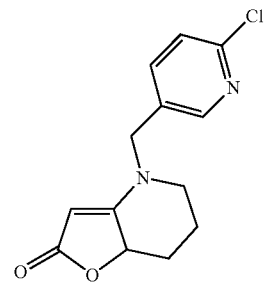

31.55 g (80.36 mmol) of 4-[[(6-chloropyridin-3-yl]methyl](3-iodopropyl)amino]furan-2(5H)-one (II-3) are dissolved in 900 ml of tetrahydrofuran and cooled to −78° C., and 42.19 ml (84.38 mmol) of a 2.0M solution of lithium diisopropylamide in tetrahydrofuran are added. After 10 minutes of stirring at −78° C., the mixture is warmed to room temperature and stirred at room temperature for a further 30 minutes. After addition of 20 ml of methanol, the mixture is concentrated under reduced pressure. Purification of the residue by column chromatography on silica gel (silica gel 60, Merck, particle size: 0.04 to 0.063 mm) using the mobile phase ethyl acetate gives 18.05 g (85% of theory) of 4-[(6-chloropyridin-3-yl)methyl]-5,6,7,7a-tetrahydrofuro[3,2-b]pyridine-2(4H)-one.

$^1$H-NMR (CD$_3$CN): δ [ppm]=1.48 (m, 1 H), 1.85-2.00 (m, 2 H), 2.32 (m, 1 H), 3.08 (m, 1 H), 3.27 (m, 1 H), 4.25 (d, 1 H), 4.40 (d, 1 H), 4.64 (s, 1 H), 4.76 (dd, 1 H), 7.37 (d, 1 H), 7.67 (dd, 1 H), 8.31 (d, 1 H).

Separation of the enantiomers of 4-[(6-chloropyridin-3-yl)methyl]-5,6,7,7a-tetrahydrofuro[3,2-b]pyridin-2(4H)-one (Example I-2) by preparative HPLC on a chiral phase.

Example I-3

X-Ray Structure Determination

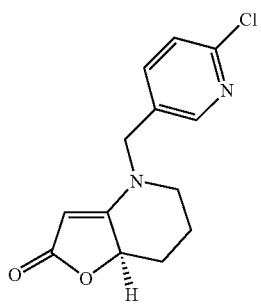

Crystals suitable for X-ray structure determination are obtained by crystallization from acetone. The lattice constants and the reflex intensities are determined using a Siemens P4 diffractometer.

The structure was resolved using direct methods (program system SHELXTL version 5.10). Using the program SHELXTL version 6.10 against F$^2$, the structure was refined.

Crystal data and refined structure:

| | |
|---|---|
| Empirical formula | C$_{13}$H$_{13}$ClN$_2$O$_2$ |
| Molar mass | 264.70 |
| Temperature | 153 K |
| Wavelength | 0.71073 Å |
| Crystal system | Monoclinic |
| Space group | P2$_1$ |
| Cell dimensions | a = 5.4002(2) Å   α = 90°. |
| | b = 8.9237(3) Å   β = 96.8250(10)°. |
| | c = 13.0576(5) Å   γ = 90°. |
| Cell volume | 624.78(4) Å3 |
| Formula units per cell Z | 2 |
| Density (calculated) | 1.407 Mg/m$^3$ |
| Absorption coefficient | 0.301 mm$^{-1}$ |
| F(000) | 276 |
| Crystal dimensions | 0.04 × 0.20 × 0.25 mm$^3$ |
| Theta range for data collection | 1.57 to 31.49°. |
| Index range | −7 <= h <= 7, −13 <= k <= 13, −19 <= l <= 19 |
| Measured reflexes | 9509 |
| Independent reflexes | 3964 [R(int) = 0.0363] |
| Completeness for theta = 31.49° | 96.6% |
| Absorption correction | SADABS (Bruker-AXS) |
| Refinement method | Full matrix smallest squares on F$^2$ |
| Data/restraints/parameters | 3964/1/173 |
| Goodness-of-fit on F2 | 1.003 |
| Final R indices [I > 2sigma(I)] | R1 = 0.0443, wR2 = 0.1084 |
| R values (all data) | R1 = 0.0478, wR2 = 0.1106 |
| Largest maximum and minimum | 0.256 and −0.387 e.Å$^{-3}$ |

Example I-4

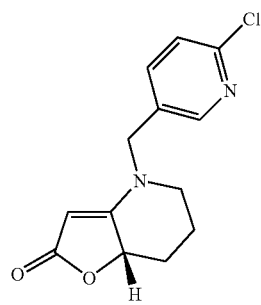

$^1$H-NMR (CDCl$_3$): δ [ppm]=1.59 (m, 1 H), 1.85-2.05 (m, 2 H), 2.44 (m, 1 H), 3.02 (m, 1 H), 3.23 (m, 1 H), 4.16 (d, 1 H), 4.36 (d, 1 H), 4.74 (dd, 1 H), 4.79 (s, 1 H), 7.36 (d, 1 H), 7.58 (dd, 1 H), 8.31 (d, 1 H).

Method 2

Example I-5

4-[(6-Chloropyridin-3-yl)methyl]-6-methylene-5,6,7,7a-tetrahydrofuro[3,2-b]-pyridin-2(4H)-one

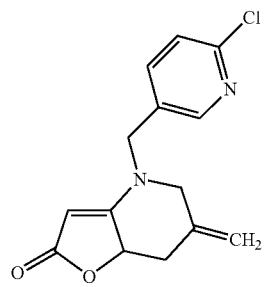

At 100° C., 540 mg (1.55 mmol) of 5-[2-({[(6-chloropyridin-3-yl)methyl]amino}methyl)prop-2-en-1-yl]-4-pyrrolidin-1-ylfuran-2(5H)-one (III-1) in 20 ml of acetic acid are stirred for 2 hours. The reaction mixture is concentrated under reduced pressure, the residue is taken up in dichloromethane and the mixture is washed with water. The aqueous phase is extracted twice with dichloromethane. The combined organic phase is washed with 1N aqueous sodium hydroxide solution, and the aqueous phase (sodium hydroxide solution) for its part is extracted twice with dichloromethane. The combined organic phase is dried over sodium sulphate and concentrated under reduced pressure. Purification of the residue by reciystallization from ethyl acetate gives 407 mg (94% of theory) of 4-[(6-chloropyridin-3-yl)methyl]-6-methylene-5,6,7,7a-tetrahydrofuro[3,2-b]pyridin-2(4H)-one.

¹H-NMR (CD₃CN): δ [ppm]=2.26 (td, 1 H), 3.08 (dd, 1 H), 3.77 (d, 1 H), 3.99 (d, 1 H), 435 (d, 1 H), 4.45 (d, 1 H), 4.65 (s, 1 H), 4.81 (dd, 1 H), 5.03 (m, 2 H), 7.37 (d, 1 H), 7.65 (dd, 1 H), 8.30 (d, 1 H).

Method 3

Example I-6

4-[(6-Chloropyridin-3-yl)methyl]-4,5,8,8a-tetrahydro-2H-furo[3,2-b]azepin-2-one

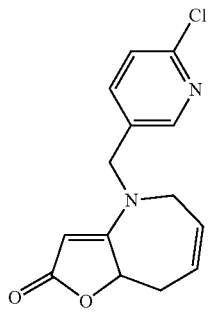

40 mg (0.13 mmol) of 5-allyl-4-{allyl[(6-chloropyridin-3-yl)methyl]amino}furan-2(5H)-one (VI-1) are dissolved in 4 ml of dichloromethane, 11 mg (0.013 mmol) of the second generation Grubbs catalyst are added and the mixture is stirred at room temperature for 2 hours. Concentration under reduced pressure and purification of the residue by column chromatography on silica gel (silica gel 60, Merck, particle size: 0.04 to 0.063 mm) using the mobile phase ethyl acetate gives 29 mg (80% of theory) of 4-[(6-chloropyridin-3-yl)methyl]-4,5,8,8a-tetrahydro-2H-furo[3,2-b]azepin-2-one.

¹H-NMR (CDCl₃): δ [ppm]=2.38 (m, 1 H), 2.97 (m, 1 H), 3.38 (dd, 1 H), 4.31 (m, 1 H), 4.39 (d, 1 H), 4.49 (d, 1 H), 4.69 (s, 1 H), 5.31 (dd, 1 H), 5.67 (m, 1 H), 5.80 (m, 1 H), 7.33 (d, 1 H), 7.53 (dd, 1 H), 8.30 (d, 1 H).

Example I-7

4-[(6-Chloropyridin-3-yl)methyl]-4,5,6,7,8,8a-hexahydro-2H-furo[3,2-b]-azepin-2-one

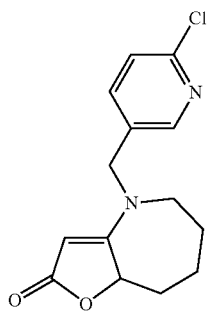

10 mg (0.036 mmol) of 4-[(6-chloropyridin-3-yl)methyl]-4,5,8,8a-tetrahydro-2H-furo[3,2-b]azepin-2-one (1-6) are dissolved in 10 ml of toluene, 5 mg (0.005 mmol) of tris(triphenylphosphine)rhodium(I) chloride and 4 mg (0.015 mmol) of triphenylphosphine are added and the mixture is hydrogenated under a hydrogen pressure of 3 bar and at 110-120° C. for 24 hours. The mixture is filtered and the filtrate is concentrated under reduced pressure. Purification of the residue by column chromatography on silica gel (silica gel 60, Merck, particle size: 0.04 to 0.063 mm) using the mobile phase mixture ethyl acetate:cyclohexane (2:1 to 4:1) gives 8 mg (79% of theory) of 4-[(6-chloropyridin-3-yl)methyl]-4,5,6,7,8,8a-hexahydro-2H-furo[3,2-b]azepin-2-one.

¹H-NMR (CDCl₃): δ [ppm]=1.40 (m, 1 H), 1.51-1.70 (m, 2 H), 1.88 (m, 1 H), 2.05 (m, 1 H), 2.40 (m, 1 H), 3.24 (dd, 1 H), 3.40 (dd, 1 H), 4.40 (m, 2 H), 4.67 (s, 1 H), 4.95 (dd, 1 H), 7.35 (d, 1 H), 7.57 (dd, 1 H), 8.30 (d, 1 H).

Method 4

Example I-8

1-[(6-Chloropyridin-3-yl)methyl]-2,3-dihydro-1H-furo[4,5-d][1,3]oxazin-5(3aH)-one

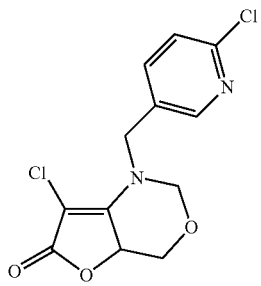

139.0 mg (0.48 mmol) of 2-chloro-5-hydroxymethyl-4-{[(6-chloropyridin-3-yl)methyl]amino}-furan-2(5H)-one (VII-1) are initially charged in a mixture of 34.75 ml of toluene and 5 ml of N,N-dimethylformamide (DMF), and 173.2 mg (5.76 mmol) of paraformaldehyde and 20.8 mg (0.11 mmol) of para-toluenesulphonic acid monohydrate. With stirring, the reaction mixture is then heated at reflux temperature on a water separator for about 18 hours. After concentration of the organic phase under reduced pressure, the residue that remains is purified by prep. HPLC (neutral). This gives 54 mg (33% of theory) of 1-[(6-chloropyridin-3-yl)methyl]-2,3-dihydro-1H-furo[4,5-d][1,3]oxazin-5(3aH)-one.

LC-MS (m/z): 301 (M⁺) C₁₂H₁₀Cl₂N₂O₃ (301.1)

¹³C-NMR with ¹H-NMR decoupling. (DMF-d₇, 400 MHz): δ [ppm]=49.2 (CH₂—N); 66.3 (CH₂—O); 70.8 (O—CH), 78.9 (N—CH₂—O—); 85.0 (=C—Cl); 133.6 (C-Py); 125.1, 139.3, 149.6 (CH-Py); 150.7 (C—Cl—Py); 158.9 (=C—); 169.5 (CO—O).

Halogenation (R²=Halogen)

Example I-9

3-Chloro-4-[(6-chloropyridin-3-ylmethyl]-5,6,7,7a-tetrahydrofuro[3,2-b]-pyridin-2(4H)-one

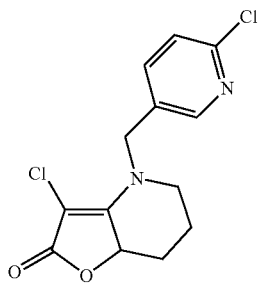

524 mg (1.98 mmol) of 4-[(6-chloropyridin-3-yl)methyl]-5,6,7,7a-tetrahydrofuro[3,2-b]pyridin-2(4H)-one (1-2) are dissolved in 20 ml of acetonitrile, then 414 μl (2.97 mmol) of triethylamine and 317 mg (2.37 mmol) of N-chlorosuccinimide are added at room temperature. After one hour of stirring, a 159 mg (1.19 mmol) of N-chlorosuccinimide are added. After a further hour of stirring, the entire reaction mixture is concentrated under reduced pressure. The residue is taken up in dichloromethane, washed successively twice with 1N aqueous hydrochloric acid, twice with 1N aqueous sodium hydroxide solution and saturated sodium chloride solution and dried over sodium sulphate. Concentration of the organic phase under reduced pressure and purification of the residue column chromatography on silica gel (silica gel 60, Merck, particle size: 0.04 to 0.063 mm) using the mobile phase mixture ethyl acetate:cyclohexane (2:1) gives 430 mg (72% of theory) of 3-chloro-4-[(6-chloropyridin-3-yl)methyl]-5,6,7,7a-tetrahydrofuro[3,2-b]pyridin-2(4H)-one.

$^1$H-NMR (CD$_3$CN): δ [ppm]=1.53 (m, 1 H), 1.83 (m, 2 H), 2.37 (m, 1 H), 3.13 (m, 1 H), 3.25 (m, 1 H), 4.79 (d, 1 H), 4.83 (dd, 1 H), 4.96 (d, 1 H), 7.43 (d, 1 H), 7.71 (dd, 1 H), 8.35 (d, 1 H).

C-Alkylation (R$^3$=alkyl)

Example I-10

4-[(6-Chloropyridin-3-yl]methyl]-7a-methyl-5,6,7,7a-tetrahydrofuro[3,2-b]-pyridin-2(4H)-one

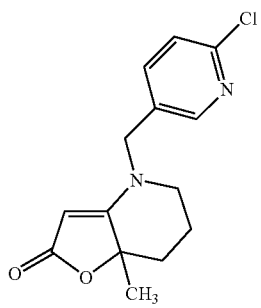

43 mg (0.16 mmol) of 4-[(6-chloropyridin-3-yl)methyl]-5,6,7,7a-tetrahydrofuro[3,2-b]pyridin-2(4H)-one (1-2) are dissolved in 2.5 ml of tetrahydrofuran, the mixture is cooled to −78° C. and 96 μl (0.16 mmol) of a 1.7M solution of tert-butyllithium in pentane are added. After 30 minutes of stirring at −78° C., 15 μl (0.24 mmol) of methyl iodide are added, and the mixture is stirred at −78° C. for a further 30 min, warmed to room temperature and stirred at room temperature for a further 3 hours. Concentration under reduced pressure and purification of the residue by column chromatography on silica gel (silica gel 60, Merck, particle size: 0.04 to 0.063 mm) using the mobile phase ethyl acetate gives 16 mg (35% of theory) of 4-[(6-chloropyridin-3-yl)methyl]-7a-methyl-5,6,7,7a-tetrahydrofuro[3,2-b]pyridin-2(4H)-one.

$^1$H-NMR (CDCl$_3$): δ [ppm]=1.57 (s, 3 H), 1.81 (m, 1 H), 1.95 (m, 2 H), 2.18 (m, 1 H), 2.92 (m, 1 H), 3.28 (m, 1 H), 4.05 (d, 1 H), 4.32 (d, 1 H), 4.76 (s, 1 H), 7.36 (d, 1 H), 7.57 (dd, 1 H), 8.30 (d, 1 H)

Formylation (R$^2$=CHO)

Example I-11

3-Formyl-4-[(6-chloropyridin-3-yl)methyl]-5,6,7,7a-tetrahydrofuro [3,2-b]-pyridin-2(4H)-one

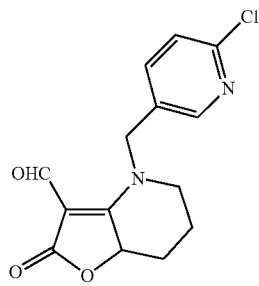

With ice-cooling, 1.89 ml (24.56 mmol) of N,N-dimethylformamide and 0.28 ml (3.02 mmol) of phosphoryl chloride are initially charged, and after one hour 500 mg (1.89 mmol) of 4-[(6-chloropyridin-3-yl)methyl]-5,6,7,7a-tetrahydrofuro [3,2-b]pyridin-2(4H)-one (1-2) are added. The mixture is then stirred at room temperature for two hours. The reaction mixture is then made alkaline using sodium carbonate, and the precipitated solid is filtered off and washed with water. This gives 0.33 g (56% of theory) of 3-formyl-4-[(6-chloropyridin-3-yl)methyl]-5,6,7,7a-tetrahydrofuro[3,2-b]pyridin-2(4H)-one.

$^1$H-NMR (CD$_3$CN): δ [ppm]=1.45 (m, 1 H), 1.71 (m, 1 H), 1.82 (m, 1 H), 2.42 (m, 1 H), 3.32 (m, 2 H), 4.78 (dd, 1 H), 5.45 (m, 2 H), 7.38 (d, 1 H), 7.65 (dd, 1 H), 8.30 (d, 1 H), 9.51 (s, 1 H).

Example I-12

4-[(6-Chloropyridin-3-yl)methyl]-6-methyl-5,6,7,7a-tetrahydrofuro[3,2-b]-pyridin-2(4H)-on

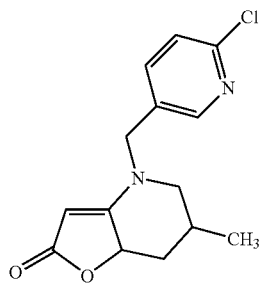

150.0 mg (0.54 mmol) of 4-[(6-chloropyridin-3-yl)methyl]-6-methylene-5,6,7,7a-tetrahydrofuro-[3,2-b]pyridin-2(4H)-one (cf. I-5) are dissolved in 75 ml of toluene, 40 mg (0.043 mmol) of tris(triphenylphosphine)rhodium(I) chloride and 15 mg (0.057 mmol) of triphenylphosphine are added and the mixture is hydrogenated under a hydrogen pressure of 3 bar and at 110-120° C. for 10 hours. The mixture is filtered and the filtrate is concentrated under reduced pressure. Purification of the residue by column chromatography on silica gel (silica gel 60, Merck, particle size: 0.04 to 0.063 mm) using the mobile phase ethyl acetate/cyclohexane (2:1 to 4:1)

gives both possible diastereomers of 4-[(6-chloropyridin-3-yl)methyl]-6-methyl-5,6,7,7a-tetrahydrofuro-[3,2-b]pyridin-2(4H)-one: (a) 85 mg (56% of theory) of diastereomer A and (b) after preparative HPLC 18 mg (12% of theory) of diastereomer B.

Example I-12a

Diastereomer A $^1$H-NMR (CD$_3$CN): δ [ppm]=0.96 (d, 3 H), 2.13 (m), 2.31 (m, 1 H), 2.68 (dd, 1 H), 3.28 (dd, 1 H), 4.19 (d, 1 H), 4.39 (d, 1 H), 4.70 (s, 1 H), 4.77 (dd, 1 H), 7.39 (d, 1 H), 7.70 (dd, 1 H), 8.32 (d, 1 H).

Example I-12b

Diastereomer B $^1$H-NMR (CD$_3$CN): δ [ppm]=0.97 (d, 3 H), 1.85-2.20 (m), 2.31 (m, 1 H), 2.99 (dd, 1 H), 3.17 (dd, 1 H), 4.39 (d, 1 H), 4.46 (d, 1 H), 4.62 (s, 1 H), 4.88 (dd, 1 H), 7.39 (d, 1 H), 7.68 (dd, 1 H), 8.31 (d, 1 H).

Example I-13

4-[(6-Chloropyridin-3-yl)methyl]-6-hydroxy-6-hydroxymethyl-5,6,7,7a-tetrahydrofuro[3,2-b]pyridin-2(4H)-one

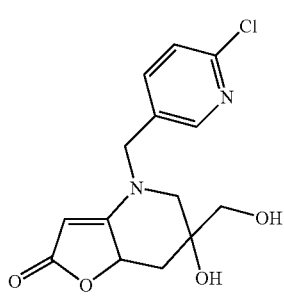

1.86 g (6.72 mmol) of 4-[(6-chloropyridin-3-yl)methyl]-6-methylene-5,6,7,7a-tetrahydrofuro-[3,2-b]pyridin-2(4H)-one (cf. I-5) are dissolved in 20 ml of tetrahydrofuran, and 5.06 ml (0.40 mmol) of a 2.5% strength solution of osmium tetroxide in tert-butanol and 1.28 g (10.08 mmol) of N-methylmorpholine N-oxide are added successively at 0° C. After 3 hours of stirring at room temperature, the mixture is substantially concentrated under reduced pressure, the residue is taken up in water and the mixture is extracted repeatedly with ethyl acetate. Concentration of the organic phase under reduced pressure gives 1.8 g of crude product (mixture of diastereomers). 200 mg of the crude product (taken into account for the determination of the yield) are purified by column chromatography on silica gel (silica gel 60, Merck, particle size: 0.04 to 0.063 mm) using the mobile phase mixture dichloromethane:methanol (95:5 to 90:10). This gives both possible diastereomers of 4-[(6-chloropyridin-3-yl)methyl]-6-hydroxy-6-hydroxymethyl-5,6,7,7a-tetrahydrofuro [3,2-b]pyridin-2(4H)-one: (a) 41 mg (18% of theory) of diastereomer A and (b) 104 mg (47% of theory) of diastereomer B.

Example I-13a

Diastereomer A $^1$H-NMR (CD$_3$CN). δ [ppm]=1.45 (t, 1 H), 2.27 (dd, 1 H), 3.09-3.29 (m), 4.30 (d, 1 H), 4.44 (d, 1 H), 4.69 (s, 1 H), 5.06 (dd, 1 H), 7.40 (d, 1 H), 7.70 (dd, 1 H), 8.32 (d, 1 H).

Example I-13b

Diastereomer B $^1$H-NMR (CD$_3$CN): δ [ppm]=1.37 (dd, 1 H), 2.53 (dd, 1 H), 3.09-3.38 (m), 4.42 (d, 1 H), 4.55 (d, 1 H), 4.61 (s, 1 H), 4.77 (dd, 1 H), 7.39 (d, 1 H), 7.75 (dd, 1 H), 8.35 (d, 1 H).

Example I-14

4-[(6-Chloropyridin-3-yl)methyl]-6-oxo-6-hydroxymethyl-5,6,7,7a-tetra-hydrofuro[3,2-b]pyridin-2(4H)-one

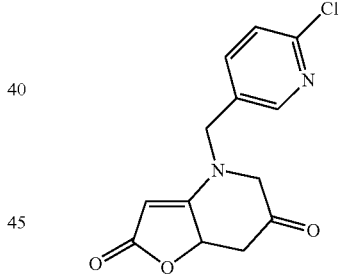

80 mg (0.26 mmol) of 4-[(6-chloropyridin-3-yl)methyl]-6-hydroxy-6-hydroxymethylene-5,6,7,7a-tetrahydrofuro[3,2-b]pyridin-2(4H)-one (cf. I-13) are dissolved in 2 ml of a mixture of dichloromethane:water (2:1), and 275 mg of sodium periodate are added at 0° C. The mixture is stirred at 0° C. for 2 hours, diluted with water and extracted four times with dichloromethane. The combined organic phases are dried over sodium sulphate and concentrated under reduced pressure. Purification of the residue by column chromatography on silica gel (silica gel 60, Merck, particle size: 0.04 to 0.063 mm) using the mobile phase ethyl acetate gives 65 mg (72% of theory) of 4-[(6-chloropyridin-3-yl)methyl]-6-oxo-6-hydroxymethyl-5,6,7,7a-tetrahydrofuro[3,2-b]pyridin-2(4H)-one.

$^1$H-NMR (CD$_3$CN): δ [ppm]=2.50 (dd, 1 H), 3.07 (dd, 1 H), 3.67 (d, 1 H), 3.98 (d, 1 H), 4.42 (d, 1 H), 4.54 (d, 1 H), 4.79 (s, 1 H), 5.21 (dd, 1 H), 7.38 (d, 1 H), 7.68 (dd, 1 H), 8.32 (d, 1 H).

Example I-15

4-[(6-Chloropyridin-3-ylmethyl]-6,6-difluor-5,6,7,7a-tetrahydrofuro[3,2-b]-pyridin-2(4H)-one

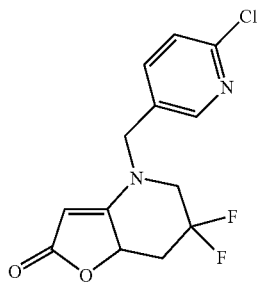

13 mg (0.047 mmol) of 4-[(6-chloropyridin-3-yl)methyl]-6-oxo-5,6,7,7a-tetrahydrofuro[3,2-b]-pyridin-2(4H)-one (cf. 1-14) are dissolved in 1 ml of dichloromethane, and 31 µl (0.23 mmol) of diethylaminosulphur trifluoride are added in two portions over a period of 30 minutes. The mixture is stirred at room temperature for one hour, saturated aqueous sodium bicarbonate solution is added and the aqueous phase is extracted with dichloromethane. The combined organic phases are dried over sodium sulphate and concentrated under reduced pressure. Purification of the residue by column chromatography on silica gel (silica gel 60, Merck, particle size: 0.04 to 0.063 mm) using the mobile phase ethyl acetate gives 8 mg (55% of theory) of 4-[(6-chloropyridin-3-yl)methyl]-6,6-difluoro-5,6,7,7a-tetrahydrofuro[3,2-b]pyridin-2(4H)-one.

$^1$H-NMR (CDCl$_3$): δ [ppm]=2.13 (dd, 1 H), 3.03 (m, 1 H), 3.38 (m, 1 H), 3.53 (m, 1 H), 4.36 (d, 1 H), 4.47 (d, 1 H), 4.89 (s, 1 H), 4.98 (dd, 1 H), 7.39 (d, 1 H), 7.57 (dd, 1 H), 8.32 (d, 1 H).

Example I-16

4-[(6-Chloropyridin-3-yl)methyl]-6-hydroxy-5,6,7,7a-tetrahydrofuro[3,2-b]-pyridin-2(4H)-one

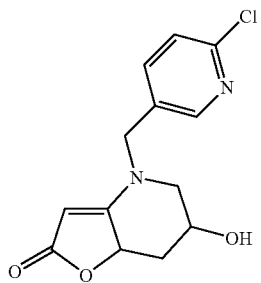

560 mg (1.61 mmol) of 4-[(6-chloropyridin-3-yl)methyl]-6-oxo-5,6,7,7a-tetrahydrofuro[3,2-b]-pyridin-2(4H)-one (Ex. 1-14) are dissolved in 14 ml of methanol, and 45 mg (1.20 mmol) of sodium borohydride are added at 0° C. The reaction mixture is stirred at 0° C. for one hour. After addition of 7.2 ml of 5% strength hydrochloric acid, the mixture is extracted with ethyl acetate. The organic phase is dried over sodium sulphate and concentrated under reduced pressure. Purification of the residue by column chromatography on silica gel (silica gel 60, Merck, particle size: 0.04 to 0.063 mm) using the solvent mixture dichloromethane:methanol (95:5) gives both possible diastereomers of 4-[(6-chloropyridin-3-yl)methyl]-6-hydroxy-5,6,7,7a-tetrahydrofuro-[3,2-b]pyridin-2(4H)-one: (a) 152 mg (34% of theory) of diastereomer A and (b) 63 mg (11% of theory) of diastereomer B.

Example I-16a

Diastereomer A $^1$H-NMR (CD$_3$CN): δ [ppm]=1.73 (m, 1 H), 2.32 (m, 1 H), 3.18 (dd, 1 H), 3.30 (m, 2 H), 4.18 (m, 1 H), 4.29 (d, 1 H), 4.42 (d, 1 H), 4.68 (s, 1 H), 5.06 (dd, 1 H), 7.40 (d, 1 H), 7.69 (dd, 1 H), 8.31 (d, 1 H).

Example I-16b (Diastereomer B)

$^1$H-NMR (CD$_3$CN): δ [ppm]=1.33 (m, 1 H), 2.75 (m, 1 H), 3.08 (dd, 1 H), 3.18 (d, 1 H), 3.38 (dd, 1 H), 4.10 (m, 1 H), 4.37 (d, 1 H), 4.50 (d, 1 H), 4.62 (s, 1 H), 4.74 (dd, 1 H), 7.39 (d, 1 H), 7.74 (dd, 1 H), 8.34 (d, 1 H).

Example I-17

4-[(6-Chloropyridin-3-yl)methyl]-6-chloro-5,6,7,7a-tetrahydrofuro[3,2-b]-pyridin-2(4H)-one and

Example I-18

4-[(6-Chloropyridin-3-yl)methyl]-7,7a-dihydrofuro[3,2-b]pyridin-2(4H)-one

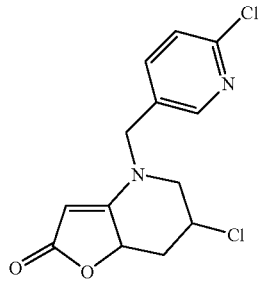

Example I-17

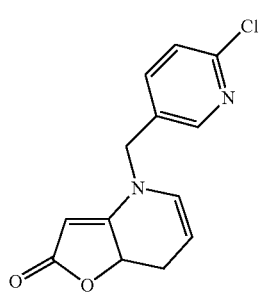

Example I-18

At 70° C., 146.0 mg (0.52 mmol) of 4-[(6-chloropyridin-3-yl)methyl]-6-hydroxy-5,6,7,7a-tetrahydrofuro[3,2-b]pyridin-2(4H)-one (cf. I-16) and 274.2 mg (1.05 mmol) of triphenylphosphine are stirred in a mixture of 2.5 ml of acetonitrile and 2.5 ml of carbon tetrachloride. After cooling to room temperature, the mixture is diluted with dichloromethane and washed successively with dilute aqueous ammonium hydroxide solution and saturated sodium chloride solution: the organic phase is dried over sodium sulphate and concentrated under reduced pressure. Purification of the residue by column chromatography on silica gel (silica gel 60, Merck, particle size: 0.04 to 063 m) using the mobile phase ethyl acetate and subsequent preparative HPLC gives both possible diastereomers of 4-[(6-chloropyridin-3-yl)methyl]-6-chloro-5,6,7,7a-tetrahydrofuro[3,2-b]pyridin-2(4H)-one: (a) 4 mg of diastereomer A (3% of theory) and (b) 15 mg of diastereomer B (9% of theory). In addition, (c) 10 mg (7% of theory) of 4-[(6-chloropyridin-3-yl)methyl]-7,7a-dihydrofuro[3,2-b]pyridin-2(4H)-one are obtained.

Example I-17a

Diastereomer A $^1$H-NMR (CD$_3$CN): δ [ppm]=2.10 (m, 1 H), 2.62 (m, 1 H), 3.45 (dd, 1 H), 3.57 (dd, 1 H), 4.30 (d, 1H), 4.45 (d, 1H), 4.54 (m, 1 H), 4.78 (s, 1 H), 5.17 (dd, 1 H), 7.40 (d, 1 H), 7.70 (dd, 1H), 8.33 (d, 1H).

Example I-17b

Diastereomer B $^1$H-NMR (CD$_3$CN): δ [ppm]=1.78 (m, 1 H), 3.03 (m, 1 H), 3.32 (dd, 1 H), 3.69 (dd, 1 H), 4.40 (d, 1H), 4.47 (m, 1H), 4.54 (d, 1 H), 4.76 (s, 1 H), 4.82 (dd, 1 H), 7.40 (d, 1 H), 7.73 (dd, 1H), 8.35 (d, 1H).

Example I-18

$^1$H-NMR (CD$_3$CN): δ [ppm]=2.21 (m, 1 H), 2.61 (m, 1 H), 4.55 (d, 1 H), 4.63 (d, 1 H), 4.85 (s, 1 H), 4.97 (dd, 1 H), 5.10 (m, 1 H), 6.16 (dd, 1 H), 7.39 (d, 1 H), 7.67 (dd, 1 H), 8.30 (d, 1 H).

Example I-19

4-[6-Chloropyridin-3-yl)methyl]-7-hydroxy-5,6,7,7a-tetrahydrofuro[3,2-b]-pyridin-2(4H)-one and Example I-20

4-[(6-Chloropyridin-3-yl)methyl]-5,6-dihydrofuro[3,2-b]pyridin-2(4H)-one

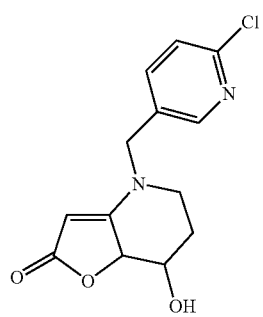

Example I-19

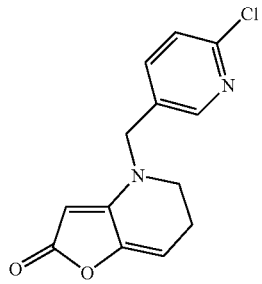

Example I-20

At room temperature, 176 mg (0.35 mmol) of tert-butyl [(6-chloropyridin-3-yl)methyl][3-hydroxy-3-(5-oxo-3-pyrrolidin-1-yl-2,5-dihydrofuran-2-yl)propyl]carbamate (cf. V-2) are stirred in a mixture of 7 ml of dichloromethane and 3.5 ml of trifluoroacetic acid for one hour. After concentration under reduced pressure, 10.5 ml of acetic acid are added to the residue, and the mixture is stirred at 100° C. for two hours. After concentration under reduced pressure, the residue is purified by column chromatography on silica gel (silica gel 60, Merck, particle size: 0.04 to 0.063 mm) using the mobile phase mixture dichloromethane:methanol (99:1 to 80:20). This gives (a) 6 mg (6% of theory) of 4-[(6-chloropyridin-3-yl)methyl]-7-hydroxy-5,6,7,7a-tetrahydrofuro-[3,2-b]pyridin-2(4H)-one as a mixture of diastereomers and (b) 30 mg (32% of theory) of 4-[(6-chloropyridin-3-yl)methyl]-5,6-dihydrofuro[3,2-b]pyridin-2(4H)-one.

Example I-19

Mixture of Diastereomers

LC-MS: m/z=281.0 [M+H]$^+$ (100%).

Example I-20

$^1$H-NMR (CD$_3$CN): δ [ppm]=2.48 (m, 2 H), 3.27 (t, 2 H), 4.41 (s, 2 H), 4.81 (s, 1 H), 5.63 (m, 1 H), 7.40 (d, 1 H), 7.72 (dd, 1 H), 8.35 (d, 1 H).

Example I-21

4-[(6-Chloropyridin-3-yl)methyl]-6,6a-dihydro-2H-furo[3,2-b]pyrrol-2,5(4H)-dione

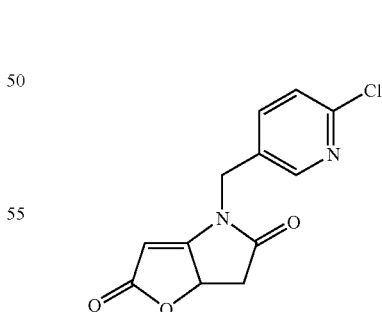

569 mg (2.17) of triphenylphosphine are added to 712 mg (1.97 mmol) of 1-[(6-chloropyridin-3-yl)methyl]-2,5-dioxopyrrolidin-3-yl bromoacetate (XI-1) in 40 ml of acetonitrile, and the mixture is stirred at 50° C. for 3 hours. 0.29 ml (2.08 mmol) of triethylamine is added, and the mixture is stirred at 50° C. for about 16 hours. The entire reaction mixture is concentrated under reduced pressure and the residue that remains is then taken up in a little ethyl acetate, the insoluble solid is filtered off and the filtrate is purified by column chromatography on silica gel (silica gel 60, Merck, particle size: 0.04 to 0.063 mm) using the mobile phase ethyl acetate. This gives 305 mg (59% of theory) of 4-[(6-chloropyridin-3-yl)methyl]-6,6a-dihydro-2H-furo[3,2-b]pyrrol-2,5(4H)-dione.

$^1$H-NMR (CDCl$_3$): δ [ppm]=2.74 (dd, 1 H), 3.16 (dd, 1 H), 4.62 (d, 1 H), 4.90 (d, 1 H), 5.18 (m, 1 H), 5.20 (s, 1 H), 7.37 (d, 1 H), 7.60 (dd, 1 H), 8.37 (d, 1 H).

The compounds (I-22) to (I-27b) listed in Table 1 below were also prepared analogously to this process.

Preparation of the Starting Materials

Compounds of the General Formula (II)

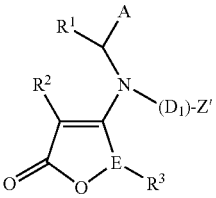

TABLE 1

$Q = O/R^1 = H$

| Ex. No. | B | R² | (D²)—Z—(D¹) | A | Physical data: ¹H-NMR, δ [ppm] |
|---|---|---|---|---|---|
| I-22 | CH₂ | H | H₂C–CH₂ (CH₂) | 5-(6-chloropyridin-3-yl) | CDCl₃, δ = 1.40 (m, 1H), 1.80-2.50 (m, 3H), 2.18 (dd, 1H), 2.60 (dd, 1H), 2.88 (m, 1H), 3.14 (m, 1H), 3.36 (m, 1H), 4.28 (d, 1H), 4.41 (d, 1H), 5.12 (s, 1H), 7.33 (d, 1H), 7.57 (dd, 1H), 8.28 (d, 1H) |
| I-23 | O | F | H₂C–CH₂ (CH₂) | 5-(6-chloropyridin-3-yl) | CDCl₃, δ = 1.54 (m, 1H), 1.87 (m, 1H), 2.00 (m, 1H), 2.42 (m, 1H), 2.95 (m, 1H), 3.12 (m, 1H), 4.32 (d, 1H), 4,63 (m, 1H), 4.65 (d, 1H), 7.38 (d, 1H), 7.63 (dd, 1H), 8.34 (d, 1H) |
| I-24 | O | H | H₂C–CH₂ (CH₂) | 5-methylthiazol-2-yl | CDCl₃, δ = 1.54 (m, 1H), 1.90 (m, 1H), 2.00 (m, 2H), 2.42 (m, 1H), 3.00 (m, 1H), 3.25 (m, 1H), 4.31 (d, 1H), 4.42 (d, 1H), 4.69 (dd, 1H), 4.83 (s, 1H), 7.46 (s, 1H) |
| I-25 | O | Br | H₂C–CH₂ (CH₂) | 5-(6-chloropyridin-3-yl) | CDCl₃, δ = 1.60 (m, 1H), 1.87 (m, 2H), 2.47 (m, 1H), 3.08 (m, 1H), 3.23 (m, 1H), 4.78 (dd, 1H), 4.89 (d, 1H), 4.98 (d, 1H), 7.39 (d, 1H), 7.64 (dd, 1H), 8.33 (d, 1H) |
| I-26 | O | Br | O–CH₂ (CH₂) | 5-(6-chloropyridin-3-yl) | CDCl₃, δ = 3.19 (m, 1H), 3.42 (m, 1H), 4.02 (m, 1H), 4.11 (m, 1H), 4.90 (d, 1H), 4.97 (d, 1H), 5.79 (s, 1H), 7.42 (d, 1H), 7.68 (dd, 1H), 8.36 (d, 1H). |
| I-27a | O | H | H₂C–CHF–CH₂ | 5-(6-chloropyridin-3-yl) | CD₃CN, δ = 1.60 (dm, 1H), 2.95 (m, 1H), 3.46 (m, 2H), 4.44 (d, 1H), 4.53 (d, 1H), 4.69 (s, 1H), 4.78 (dd, 1H), 5.04 (dm, 1H), 7.39 (d, 1H), 7.71 (dd, 1H), 8.33 (d, 1H) |
| I-27b | O | H | H₂C–CHF–CH₂ | 5-(6-chloropyridin-3-yl) | CD₃CN, δ = 1.82 (ddd, 1H), 2.66 (m, 1H), 3.45 (m, 2H), 4.28 (d, 1H), 4.43 (d, 1H), 4.76 (s, 1H), 5.02 (dd, 1H), 5.14 (dm, 1H), 7.41 (d, 1H), 7.69 (dd, 1H), 8.32 (d, 1H) |

Example II-1

4-[[(6-Chloropyridin-3-yl)methyl](2-hydroxyethyl)amino]furan-2(5H)-one ($R^1$=H, -($D^1$)-Z'=$CH_2CH_2$—OH; $R^2$=H; E-$R^3$=$CH_2$, A=6-chloropyrid-3-yl)

2.41 g (24.11 mmol) of tetronic acid and 28 mg (0.16 mmol) of 4-toluenesulphonic acid are added to 3.00 g (16.07 mmol) of 2-{[(6-chloropyridin-3-yl)methyl]amino}ethanol (cf. WO 2005055715 A2) in 150 ml of toluene, and the mixture is heated under reflux on a water separator for 3 hours. After cooling of the reaction mixture, the liquid phase is decanted and the solid residue is purified by column chromatography on silica gel (silica gel 60, Merck, particle size: 0.04 to 0.063 mm) using the mobile phase mixture dichloromethane:methanol (95:5). This gives 722 mg (16% of theory) of 4-[(6-chloropyridin-3-yl)methyl](2-hydroxyethyl)amino]furan-2(5H)-one.

$^1$H-NMR ($CD_3CN$): δ [ppm]=2.88 (t, 1 H), 3.28 (t, 2 H), 3.66 (q, 2 H), 4.50 (s, 2 H), 4.58 (s, 1 H), 4.82 (s, 2 H), 7.37 (d, 1 H), 7.65 (dd, 1 H), 8.28 (d, 1 H).

Example II-2

4-[(3-Chloropropyl)[(6-chloropyridin-3-yl)methyl]amino]furan-2(5H)-one ($R^1$=H, -($D^1$)-Z'=$CH_2CH_2CH_2$—Cl; $R^2$=H; E-$R^3$=$CH_2$, A=6-chloropyrid-3-yl)

4.26 ml (74.4 mmol) of acetic acid are added to 16.30 g (74.4 mmol) of 3-chloro-N-[(6-chloropyridin-3-yl)methyl]propan-1-amine (IVa-1 cf. also B. Latli et al. J. Med. Chem. 1999, 42, 2227-2234) in 300 ml of benzene, and the mixture is stirred at room temperature for 30 minutes. 9.68 g (96.7 mmol) of tetronic acid and 128 mg of 4-toluenesulphonic acid are then added, and the mixture is heated under reflux on a water separator for 2 hours. The reaction mixture is concentrated under reduced pressure, the residue is then taken up in the solvent mixture dichloromethane:methanol (95:5) and the mixture is washed successively with 1N hydrochloric acid, 1N aqueous sodium hydroxide solution and saturated sodium chloride solution and dried over sodium sulphate. Concentration of the organic phase under reduced pressure and purification of the residue by column chromatography on silica gel (silica gel 60, Merck, particle size: 0.04 to 0.063 mm) using the mobile phase ethyl acetate gives 9.15 g (33% of theory) of 4-[(3-chloropropyl)[(6-chloropyridin-3-yl)methyl]amino]furan-2(5H)-one.

$^1$H-NMR ($CDCl_3$): δ [ppm]=2.07 (m, 2 H), 3.38 (t, 3 H), 3.58 (t, 2 H), 4.40 (s, 2 H), 4.81 (s, 1 H), 4.82 (s, 2 H), 7.38 (d, 1 H), 7.52 (dd, 1 H), 8.28 (d, 1 H).

Example II-3

4-[[(6-Chloropyridin-3-yl)methyl] (3-iodopropyl)amino]furan-2(5H)-one ($R^1$=H, -($D^1$)-Z'=$CH_2CH_2CH_2$—I; $R^2$=H; E-$R^3$=$CH_2$, A=6-chloropyrid-3-yl)

27.50 g (91.3 mmol) of 4-[(3-chloropropyl)[(6-chloropyridin-3-yl)methyl]amino]furan-2(5H)-one (I-2) and 51.60 g (344.2 mmol) of sodium iodide in 1.2 l of acetonitrile are heated under reflux for 4 hours. Concentration of the organic phase under reduced pressure and purification of the residue by column chromatography on silica gel (silica gel 60, Merck, particle size: 0.04 to 0.063 mm) using the mobile phase ethyl acetate gives 31.5 g of 4-[[(6-chloropyridin-3-yl)methyl](3-iodopropyl)amino]furan-2(5H)-one.

$^1$H-NMR ($CDCl_3$): δ [ppm]=2.10 (m, 2 H), 3.18 (t, 3 H), 3.31 (t, 2 H), 4.41 (s, 2 H), 4.81 (s, 1 H), 4.83 (s, 2 H), 7.38 (d, 1 H), 7.53 (dd, 1 H), 8.28 (d, 1 H).

Compounds of the General Formula HN(R')—$CH_2$-A (IVa)

Example IVa-1

3-Chloro-N-[(6-chloropyridin-3-yl)methyl]propan-1-amine (R'=$CH_2CH_2CH_2$—Cl, A=6-chloropyrid-3-yl) (cf. B. Latli et al. J. Med. Chem. 1999, 42, 2227-2234)

16.20 g (100 mmol) of 2-chloro-5-(chloromethyl)pyridine, 16.90 g (130 mmol) of 3-chloropropan-1-amine hydrochloride and 36.24 ml (260 mmol) of triethylamine in 200 ml acetonitrile stirred at 60° C. for 20 hours. After addition of 30.67 g (230 mmol) of 30 percent strength aqueous sodium hydroxide solution, the reaction mixture is concentrated under reduced pressure and the residue is extracted with chloroform. Concentration of the extract under reduced pressure gives 19.03 g (87% of theory) of 3-chloro-N-[(6-chloropyridin-3-yl)methyl]propan-1-amine which can be used without further purification for the next reaction (cf. Ex. II-2).

$^1$H-NMR ($CD_3CN$): δ [ppm]=1.85-2.05 (m, 2 H), 2.69 (t, 2 H), 3.65 (t, 2 H), 3.75 (s, 2 H), 7.32 (d, 1 H), 7.71 (dd, 1 H), 8.30 (d, 1 H).

Example IVa-2

3-{[(6-Chloropyridin-3-yl)methyl]amino}propan-1-ol (R'=$CH_2CH_2CH_2$—OH, A=6-chloropyrid-3-yl) (cf. EP 192060 A1)

At room temperature, 14.16 g (100 mmol) of 6-chloronicotinaldehyde and 8.41 ml (110 μmol) of 3-aminopropanol are stirred in 100 ml of ethanol for 30 minutes. A little at a time 3.78 g (100 mmol) of sodium borohydride are added, and the mixture is stirred at room temperature for about 16 hours. After concentration under reduced pressure, water and calcium carbonate are added and the mixture is extracted with methyl tert-butyl ether. The combined organic phase is dried over sodium sulphate and concentrated under reduced pressure. Column chromatography of the residue on silica gel (silica gel 60, Merck, particle size: 0.04 to 0.063 mm) using the mobile phase mixture dichloromethane:methanol (95:5) gives 3.86 g (19% of theory) of 3-{[(6-chloropyridin-3-yl)methyl]amino}propan-1-ol.

$^1$H-NMR ($CD_3CN$): δ [ppm]=1.65 (m, 2 H), 2.68 (t, 2 H), 3.59 (t, 2 H), 3.74 (s, 2 H), 7.32 (d, 1 H), 7.70 (dd, 1 H), 8.30 (d, 1 H).

Compounds of the General Formula (V)

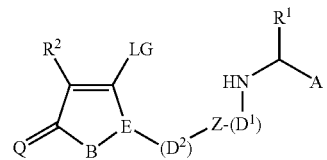

Example V-1

5-[2-({[(6-Chloropyridin-3-yl)methyl]amino}methyl)prop-2-en-1-yl]-4-pyrrolidin-1-ylfuran-2(5H)-one ($R^1$, $R^2$=H; B, Q=O; E-($D^2$)-Z-($D^1$)=CHCH$_2$C(=CH$_2$)CH$_2$—; LG=N-pyrrolidino; A=6-chloropyrid-3-yl)

At 60° C., 600 mg (2.48 mmol) of 5-[2-(chloromethyl)prop-2-en-1-yl]-4-pyrrolidin-1-ylfuran-2(5H)-one (V-1a), 354 mg (2.48 mmol) of 1-(6-chloropyridin-3-yl)methanamine and 0.43 ml (2.48 mmol) of N-ethyl-N-isopropylpropan-2-amine in 10 ml of acetonitrile are stirred for 21 hours. Concentration under reduced pressure and purification of the residue by column chromatography on silica gel (silica gel 60, Merck, particle size: 0.04 to 0.063 mm) using the mobile phase mixture dichloromethane:methanol (98:2 to 90:10) gives 650 mg (73% of theory) of 5-[2-({[(6-chloropyridin-3-yl)methyl]amino}methyl)prop-2-en-1-yl]-4-pyrrolidin-1-ylfuran-2(5H)-one.

$^1$H-NMR (CD$_3$CN): δ [ppm]=1.85 (m, 2 H), 1.96 (m, 2 H), 2.26 (dd, 1 H), 2.80 (dd, 1 H), 3.15 (m, 2 H), 3.18 (d, 1 H), 3.24 (d, 1 H), 3.39 (m, 2 H), 3.70 (s, 2 H), 4.37 (s, 1 H), 4.97 (s, 1 H), 5.05 (dd, 1 H), 5.09 (s, 1 H), 7.34 (d, 1 H), 7.72 (dd, 1 H), 8.30 (d, 1 H).

V-1a 5-[2-(Chloromethyl)prop-2-en-1-yl]-4-pyrrolidin-1-ylfuran-2(5H)-one 800 mg (5.22 mmol) of 4-pyrrolidin-1-ylfuran-2(5H)-one (Shandala, M. Y. et al. J. Heterocycl. Chem. 1984, 21, 1753-1754) are dissolved in 80 ml of tetrahydrofuran and cooled to −78° C., and 3.07 ml (5.22 mmol) of a 1.7M solution of tert-butyllithium in pentane are added. After 30 min of stirring at −78° C., 1.21 ml (10.45 mmol) of 3-chloro-2-(chloromethyl)prop-1-ene are added and the mixture is stirred at −78° C. for a further 30 minutes, warmed to room temperature over a period of about 16 hours and stirred at room temperature for a further 3 hours. After addition of methanol and concentration under reduced pressure, the residue is purified by column chromatography on silica gel (silica gel 60, Merck, particle size: 0.04 to 0.063 mm) using the mobile phase ethyl acetate. This gives 735 mg (57% of theory) of 5-[2-(chloromethyl)prop-2-en-1-yl]-4-pyrrolidin-1-ylfuran-2(5H)-one.

$^1$H-NMR (CD$_3$CN): δ [ppm]=1.85-2.05 (m, 4 H), 2.42 (dd, 1 H), 2.91 (dd, 1 H), 3.32 (m, 4 H), 4.15 (d, 1 H), 4.20 (d, 1 H), 4.40 (s, 1 H), 5.05 (dd, 1 H), 5.14 (s, 1 H), 5.31 (s, 1 H).

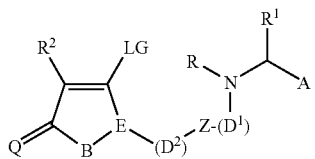

Example V-2 tert-Butyl [(6-chloropyridin-3-yl)methyl][3-hydroxy-3-(5-oxo-3-pyrrolidin-1-yl-2,5-dihydrofuran-2-yl)propyl]carbamate ($R^1$, $R^2$=H; B, Q=O; E-($D^2$)-Z-($D^1$)-NR=CHCH(OH)CH$_2$CH$_2$—N-(tert-butoxycarbonyl)-(BOC); LG=N-pyrrolidino; A=6-chloropyrid-3-yl)

1.23 g (8.06 mmol) of 4-pyrrolidin-1-ylfuran-2(5H)-one (Shandala, M. Y. et al. J. Heterocycl. Chem. (1984), 21, 1753-1754) are dissolved in 30 ml of tetrahydrofuran and cooled to −78° C., and 6.17 ml (10.48 mmol) of a 1.7M solution of tert-butyllithium in pentane are added. After 30 min of stirring at −78° C., a solution of 2.65 g (8.87 mmol) tert-butyl [(6-chloropyridin-3-yl)methyl](3-oxopropyl)carbamate in 10 ml of tetrahydrofuran are added, and the mixture is stirred at −78° C. for 1 hour. After addition of methanol and concentration under reduced pressure, the residue is purified by column chromatography on silica gel (silica gel 60, Merck, particle size: 0.04 to 0.063 mm) using the mobile phase mixture dichloromethane:methanol (95:5). This gives 2.67 g (57% of theory) of tert-butyl [(6-chloropyridin-3-yl)methyl] [3-hydroxy-3-(5-oxo-3-pyrrolidin-1-yl-2,5-dihydrofuran-2-yl)propyl]carbamate as a mixture of diastereomers which can be used without further purification for the next reaction (cf. Ex. I-19 and 1-20).

LC-MS: m/z=451.9 [M+H]$^+$ (100%).

V-2a tert-Butyl [(6-chloropyridin-3-yl)methyl](3-hydroxypropyl)carbamate 2.00 g (9.97 mmol) of 3-{[(6-chloropyridin-3-yl)methyl]amino}propan-1-ol (cf. EP 192060 A1 and Ex. IVa-2) are dissolved in 24 ml of tetrahydrofuran, and 10.72 ml (10.72 mmol) of 1N aqueous sodium hydroxide solution and 2.18 g (9.97 mmol) of di-tert-butyl dicarbonate are added in succession. The mixture is stirred at room temperature for 1 hour and most of the tetrahydrofuran is removed under reduced pressure. The aqueous phase that remains is acidified with sodium hydrogen sulphate (>pH 2) and extracted with ethyl acetate. The combined organic phase is dried over sodium sulphate and concentrated under reduced pressure. This gives 3.00 g of tert-butyl [(6-chloropyridin-3-yl)methyl](3-hydroxypropyl)carbamate (100% of theory) which can be used without further purification for the next reaction.

V-2b tert-Butyl [(6-chloropyridin-3-yl)methyl](3-oxopropyl)carbamate 3.00 g (9.97 mmol) of tert-butyl [(6-chloropyridin-3-yl)methyl](3-hydroxypropyl)carbamate are dissolved in 50 ml of dichloromethane, 56.38 g (19.94 mmol) of a 15 percent strength solution of Dess-Martin periodinane in dichloromethane are added and the mixture is stirred at room temperature for 1 hour. The reaction mixture is washed with 1N aqueous sodium hydroxide solution and the aqueous phase is extracted with dichloromethane. The combined organic phases are dried over sodium sulphate and concentrated under reduced pressure. Purification of the residue by column chromatography on silica gel (silica gel 60, Merck, particle size: 0.04 to 0.063 mm) using the mobile phase mixture ethyl acetate:cyclohexane (1:1) gives 2.75 g (92% of theory) of tert-butyl [(6-chloropyridin-3-yl)methyl](3-oxopropyl)carbamate.

$^1$H-NMR (CD$_3$CN): δ [ppm]=1.41 (s, 9 H), 2.62 (t, 2 H), 3.50 (t, 2 H), 4.40 (s, 2 H), 7.34 (d, 1 H), 7.63 (dd, 1 H), 8.26 (d, 1 H), 9.67 (s, 1 H).

Compounds of the General Formula (VI)

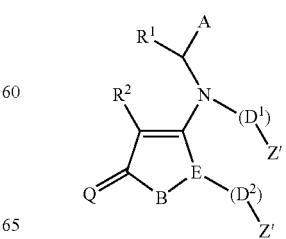

Example VI-1

5-Allyl-4-{allyl[(6-chloropyridin-3-yl)methyl]amino}furan-2(5H)-one ($R^1$=H, -($D^1$)-$Z'$=$CH_2CH$=$CH_2$; $R^2$=H; E-($D^2$)-$Z'$=CH—$CH_2CH$=$CH_2$, A=6-chloropyrid-3-yl)

500 mg (1.89 mmol) of 4-{allyl[(6-chloropyridin-3-yl)methyl]amino}furan-2(5H)-one (cf. WO 9200964 A1) are dissolved in 30 ml of tetrahydrofuran and cooled to –78° C., and 1.11 ml (1.89 mmol) of a 1.7M solution of tert-butyllithium in pentane are added. After 30 minutes of stirring at –78° C., 163 µl (1.89 mmol) of allyl bromide are added, the mixture is stirred at –78° C. for a further 30 min and warmed to room temperature, and stirring at room temperature is continued for a further 2 hours. After addition of methanol, the mixture is concentrated under reduced pressure. The residue is purified by column chromatography on silica gel (silica gel 60, Merck, particle size: 0.04 to 0.063 mm) using the mobile phase mixture ethyl acetate:cyclohexane (5:1). This gives 336 mg (64% of theory) of 5-allyl-4-{allyl[(6-chloropyridin-3-yl)methyl]amino}furan-2(5H)-one.

$^1$H-NMR ($CDCl_3$): δ [ppm]=2.42 (m, 1 H), 2.78 (m, 1 H), 3.80 (m, 2 H), 4.37 (d, 1 H); 4.43 (d, 1 H), 4.77 (s, 1 H), 5.05 (dd, 1 H), 5.17-5.28 (m, 3 H), 5.34 (d, 1 H), 5.78 (m, 2 H), 7.35 (d, 1 H), 7.54 (dd, 1 H), 8.28 (d, 1 H).

Compounds of the General Formula (VII)

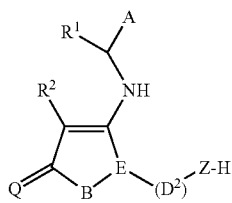

Example VII-1

3-Chloro-5-hydroxymethyl-4-{[(6-chloropyridin-3-yl)methyl]amino}furan-2(5H)-one ($R^1$=H, $R^2$=Cl; B, Q=O; E-($D^2$)-Z-H=$CHCH_2OH$, A=6-chloropyrid-3-yl)

126.0 mg (0.49 mmol) of 5-hydroxymethyl-4-{[(6-chloropyridin-3-yl)methyl]amino}furan-2(5H)-one (VII-1b) are stirred in 7.5 ml of acetonitrile, and 0.10 ml of triethylamine and 118.9 mg (0.89 mmol) of N-chlorosuccinimide are added successively at room temperature. The reaction mixture is then stirred at room temperature for 1 hour. The entire reaction mixture is then concentrated under reduced pressure to a volume of about 2 ml and purified by preparative HPLC (neutral). This gives 76.4 mg (38.4% of theory) of 3-chloro-5-hydroxymethyl-4-{[(6-chloropyridin-3-yl)methyl]amino}furan-2(5H)-one.

LC-MS (m/z): 289 ($M^+$) $C_{11}H_{10}Cl_2N_2O_3$ (289.1)

VII-1a 4-Hydroxy-5-hydroxymethylfuran-2(5H)-one 386.0 mg (1.75 mmol) of 5-benzyloxymethyl-4-hydroxyfuran-2(5H)-one (Aragon, D. T. et al., J. Org. Chem. 68, 3363-3365, 2003) are initially charged in 19.3 ml of ethanol, 38.6 mg (0.27 mmol) of Pd(OH)$_2$/C (20%) are added and the mixture is hydrogenated at room temperature until the hydrogen uptake has stopped. Removal of the catalyst by filtration and evaporation of the solvent gives 216 mg (94.7% of theory) of 4-hydroxy-5-hydroxymethylfuran-2(5H)-one which can be used without further purification for a subsequent reaction.

LC-MS (m/z): 131 ($M^+$+H)$CH_6O_4$ (130.1)

VII-1b 5-Hydroxymethyl-4-{[(6-chloropyridin-3-yl)methyl]amino}furan-2(5H)-one 905.0 mg (6.95 mmol) of 4-hydroxy-5-hydroxymethylfuran-2(5H)-one (VII-1a) and 991.8 mg (6.95 mmol) of 3-aminomethyl-6-chloropyridine are stirred in the mixture of 100.5 ml of toluene and 10 ml of N,N-dimethylformamide (DMF), and 10 mg of para-toluenesulphonic acid and 0.5 ml of acetic acid are added. With stirring, the entire reaction mixture is then heated at reflux on a water separator for about 18 hours. Concentration under reduced pressure and purification of the residue by column chromatography on silica gel (silica gel 60, Merck, particle size: 0.04 to 0.063 mm; mobile phase: cyclohexane/acetone=1:1) gives 394.2 mg (22.2% of theory) of 5-hydroxymethyl-4-{[(6-chloropyridin-3-yl)methyl]amino}furan-2(5H)-one.

LC-MS (m/z): 255 ($M^+$) $C_{11}H_{11}ClN_2O_3$ (254.6)

Compounds of the General Formula G-$CH_2$-A (X)

X-1 (5,6-Dichloropyridin-3-yl)methanol (G=OH, A=5,6-dichloropyrid-3-yl) (R. Graf et al. J. Prakt. Chem. 1932, 134, 177-87)

At 0° C., 859 ml (859 mmol) of a 1M solution of borane/tetrahydrofuran complex in tetrahydrofuran are added dropwise to 110 g (573 mmol) of 5,6-dichloronicotinic acid in 250 ml of tetrahydrofuran. The mixture is warmed to room temperature and stirred at this temperature for 3 hours. After cooling to 0° C., the reaction mixture is made alkaline using saturated aqueous potassium carbonate solution, most of the tetrahydrofuran is removed on a rotary evaporator and the residue is extracted repeatedly with ethyl acetate. The combined organic phases are washed with water and saturated aqueous sodium chloride solution and dried over sodium sulphate. Concentration of the organic phase under reduced pressured and purification of the residue by column chromatography on silica gel (silica gel 60—Merck, particle size: 0.04 to 0.063 mm) using the mobile phase mixture ethyl acetate:cyclohexane (1:2) gives 62 g (61% of theory) of (5,6-dichloropyridin-3-yl)methanol.

$^1$H-NMR ($CD_3CN$): δ [ppm]=3.31 (t, 1 H), 4.60 (d, 2 H), 7.85 (s, 1 H), 8.26 (s, 1 H)

The compound (X-1) of Table 3 was also prepared analogously to the procedure for the compound (X-5).

X-2 3-Bromomethyl-5,6-dichloropyridin (G=Br, A=5,6-dichloropyrid-3-yl) (cf. WO 2000046196 A1)

At 0° C., 16.40 g (65.52 mmol) of triphenylphosphine and 11.66 g (65.50 mmol) of N-bromosuccinimide are added to a solution of 10.60 g (59.55 mmol) of (5,6-dichloropyridin-3-yl)methanol (X-1) in 100 ml of dichloromethane. After 2 h, the reaction mixture is substantially concentrated and the residue is purified by column chromatography on silica gel (silica gel 60-Merck, particle size: 0.04 to 0.063 mm) using the mobile phase mixture ethyl acetate:cyclohexane (1:5). This gives 12.4 g (86% of theory) of 3-bromomethyl-5,6-dichloropyridine.

$^1$H-NMR ($CD_3CN$): δ [ppm]=4.53 (s, 2 H), 7.97 (s, 1 H), 8.35 (s, 1 H)

The compounds (X-6) to (X-8) from Table 3 were also prepared analogously to the procedure for the compound (X-2).

X-3 3-Bromomethyl-6-chloro-5-iodopyridine (C═Br, A=6-chloro-5-iodopyrid-3-yl)

4.60 g (18.15 mmol) of 6-chloro-5-iodo-3-methylpyridine (Setliff et al., J. Chem. Engineering Data (1976), 21(2), 246-7), 3.39 g (19.06 mmol) of N-bromosuccinimide and 0.30 g (1.82 mmol) of 2,2'-azobis(2-methylpropionitrile) in 500 ml of chlorobenzene are boiled under reflux for about 16 hours. The reaction mixture is washed with saturated aqueous sodium sulphite solution and sodium bicarbonate solution and then dried over sodium sulphate and concentrated under reduced pressure. Column cluomatography of the residue on silica gel (silica gel 60—Merck, particle size: 0.04 to 0.063 mm) using the mobile phase mixture ethyl acetate:cyclohexane (1:10) gives 3.86 g (38% of theory) of 3-bromomethyl-6-chloro-5-iodopyridine.

$^1$H-NMR (CD$_3$CN): δ [ppm]=4.48 (s, 2 H), 8.30 (s, 1 H), 8.40 (s, 1 H)

The compound (X-9) from Table 3 was also prepared analogously to the procedure for the compound (X-3).

X-4 6-Chloro-3-chloromethyl-5-fluoropyridine (G=Cl, A=6-chloro-5-fluoropyrid-3-yl)

1.00 g (6.87 mmol) of 6-chloro-5-fluoro-3-methylpyridine (F. L. Setliff, Organic Preparations and Procedures International 1971, 3, 217-222), 1.01 g (7.56 mmol) of N-chlorosuccinimide and 0.11 g (0.69 mmol) of 2,2'-azobis(2-methylpropionitrile) in 100 ml of chlorobenzene are boiled under reflux for 2 days. After about 16 hours and 32 hours, in each case a further 1.01 g (7.56 mmol) of N-chlorosuccinimide and 0.11 g (0.69 mmol) of 2,2'-azobis(2-methylpropionitrile) are added. The reaction mixture is washed with saturated aqueous sodium sulphite solution and sodium bicarbonate solution and then dried over sodium sulphate and concentrated under reduced pressure. Column chromatography of the residue on silica gel (silica gel 60—Merck, particle size: 0.04 to 0.063 mm) using the mobile phase mixture ethyl acetate:cyclohexane (1:20) gives 0.65 g (53% of theory) of 6-chloro-3-chloromethyl-5-fluoropyridine.

$^1$H-NMR (CD$_3$CN): δ [ppm]=4.68 (s, 2 H), 7.69 (d, 1 H), 8.27 (s, 1 H)

Further compounds (X-5) to (X-10) of the formula (X) are listed in Table 3 below.

TABLE 3

| | G—CH$_2$—A (X) | | |
|---|---|---|---|
| Ex. No. | G | A | Physical data$^{a)}$ |
| X-5 | OH | 3-Cl, 2-Br-pyridin-5-yl | 3.30 (t, 1H), 4.59 (d, 2H), 7.83 (s, 1H), 8.26 (s, 1H) |
| X-6 | Br | 3-CH$_3$, 2-Cl-pyridin-5-yl | 2.37 (s, 3H), 4.52 (s, 2H), 7.70 (s, 1H), 8.24 (s, 1H) |
| X-7 | Br | 3-Br, 2-Cl-pyridin-5-yl | 4.52 (s, 2H), 8.10 (s, 1H), 8.38 (s, 1H) |
| X-8 | Br | 3-Cl, 2-Br-pyridin-5-yl | 4.52 (d, 2H), 7.92 (s, 1H), 8.35 (s, 1H) |
| X-9 | Br | 3-Br, 2-Br-pyridin-5-yl | 4.50 (s, 2H), 8.07 (s, 1H), 8.37 (s, 1H) |
| X-10 | Br | 3-F, 2-Br-pyridin-5-yl | 4.55 (s, 2H), 7.65 (d, 1H), 8.27 (s, 1H) |

$^{a)}$ $^1$H-NMR (CD$_3$CN), δ [ppm]

Compounds of the General Formula (XI)

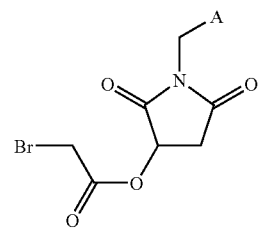

Example XI-1

1-[(6-Chloropyridin-3-yl)methyl]-2,5-dioxopyrrolidin-3-yl bromoacetate (A=6-chloropyrid-3-yl)

1.34 g (5.56 mmol) of 1-[(6-chloropyridin-3-yl)methyl]-3-hydroxypyrrolidin-2,5-dione (XI-1a) and 674 μl (8.34 mmol) of pyridine are dissolved in 15 ml of dichloromethane, and 1.12 g (5.56 mmol) of bromoacetyl bromide are added at 0° C. The mixture is stirred at room temperature for 30 minutes, and ice-water is then added. The organic is washed successively with saturated sodium bicarbonate solution and saturated sodium chloride solution, dried over magnesium sulphate and concentrated under reduced pressure. Purification of the residue by column chromatography on silica gel (silica gel 60, Merck, particle size: 0.04 to 0.063 mm) using the mobile phase mixture dichloromethane:methanol (97:3) gives 1.44 g (55% of theory) of 1-[(6-chloropyridin-3-yl)methyl]-2,5-dioxopyrrolidin-3-yl bromoacetate.

$^1$H-NMR (CDCl$_3$): δ [ppm]=2.75 (dd, 1 H), 3.22 (dd, 1 H), 3.90 (s, 2 H), 4.69 (s, 2 H), 5.50 (dd, 1 H), 7.31 (d, 1 H), 7.71 (dd, 1 H), 8.44 (d, 1 H).

XI-1a 1-[(6-Chloropyridin-3-yl)methyl]-3-hydroxy-pyrrolidine-2,5-dione 4.53 g (33.79 mmol) of D,L-malic acid and 5.30 g (37.17 mmol) of 1-(6-chloropyridin-3-yl)-methanamine in 40 ml of xylene are heated under reflux for 2 hours. After cooling to room temperature, the mixture is decanted and the residue is concentrated under reduced pressure. 8.30 g (100% of theory) of 1-[(6-chloropyridin-3-yl)methyl]-3-hydroxypyrrolidine-2,5-dione, which can be used in the next reaction without further purification, are obtained as a crude product.

$^1$H-NMR (CDCl$_3$): δ [ppm]=2.71 (dd, 1 H), 2.92 (br. s., 1 H), 3.10 (dd, 1 H), 4.65 (m, 1 H), 4.66 (s, 2 H), 7.30 (d, 1 H), 7.71 (dd, 1 H), 8.44 (d, 1 H).

BIOLOGICAL EXAMPLES

Example No. 1

Myzus Test (MYZUPE Spray Treatment)
 Solvents: 78 parts by weight of acetone
 1.5 parts by weight of dimethylformamide
 Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) which are infested by all stages of the green peach aphid (*Myzus persicae*) are sprayed with a preparation of active compound of the desired concentration.

After the desired period of time, the effect in % is determined. 100% means that all aphids have been killed; 0% means that none of the aphids have been killed.

On this test, for example, the following compounds of the Preparation Examples show good activity: see table

| Example | Active compound concentration in g/ha | Kill rate in % after 5 days |
| --- | --- | --- |
| Example I-1 | 500 | 100 |
| Example I-2 | 500 | 100 |
| Example I-3 | 500 | 100 |
| Example I-4 | 500 | 100 |
| Example I-6 | 500 | 100 |
| Example I-7 | 500 | 100 |
| Example I-8 | 500 | 100 |
| Example I-9 | 500 | 100 |
| Example I-10 | 500 | 100 |
| Example I-11 | 500 | 100 |
| Example I-12a | 500 | 100 |
| Example I-12b | 500 | 100 |
| Example I-14 | 500 | 100 |
| Example I-15 | 500 | 100 |
| Example I-17a | 500 | 100 |
| Example I-17b | 500 | 90 |
| Example I-18 | 500 | 100 |
| Example I-19 | 500 | 100 |
| Example I-20 | 500 | 100 |
| Example I-22 | 500 | 100 |
| Example I-23 | 500 | 100 |
| Example I-24 | 500 | 100 |
| Example I-25 | 500 | 100 |
| Example I-27a | 500 | 100 |
| Example I-27b | 500 | 100 |

Example No. 2

Myzus Test; Oral; (MYZUPE O)
 Solvent: 80 parts by weight of acetone

To produce a suitable preparation of active compound, 1 part by weight of active compound is mixed with the stated amounts of solvent and emulsifier, and the concentrate is diluted with water to the desired concentration.

Containers are populated with all stages of the green peach aphid (*Myzus persicae*), the treatment is by sucking at the preparation of active compound of the desired concentration.

After the desired period of time, the effect in % is determined. 100% means that all aphids have been killed; 0% means that none of the aphids have been killed.

In this test, for example, the following compounds of the Preparation Examples show good activity: see table

| Example | Active compound concentration in ppm | Kill rate in % after 5 days |
| --- | --- | --- |
| Example I-1 | 100 | 100 |
| Example I-12a | 100 | 100 |
| Example I-12b | 100 | 100 |
| Example I-14 | 100 | 100 |

Example No. 3

*Spodoptera frugiperda* Test (SPODFR Spray Treatment)
 Solvents: 78 parts by weight of acetone
 1.5 parts by weight of dimethylformamide
 Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of maize leaves (*Zea mays*) are sprayed with a preparation of active compound of the desired concentration and, after drying, populated with caterpillars of the armyworm (*Spodoptera frugiperda*).

After the desired period of time, the effect in % is determined. 100% means that all caterpillars have been killed; 0% means that none of the caterpillars have been killed.

In this test, for example, the following compounds of the Preparation Examples show good activity: see table

| Example | Active compound concentration in g/ha | Kill rate in % after 7 days |
| --- | --- | --- |
| Example I-2 | 500 | 100 |
| Example I-3 | 500 | 100 |

Example No. 4

*Phaedon cochleariae* Test (PHAECO Spray Treatment)

Solvents: 78 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with a preparation of active compound of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the Preparation Examples show good activity: see table

| Example | Active compound concentration in g/ha | Kill rate in % after 7 days |
| --- | --- | --- |
| Example I-3 | 500 | 100 |
| Example I-4 | 500 | 100 |
| Example I-17a | 500 | 100 |
| Example I-20 | 500 | 100 |
| Example I-23 | 500 | 100 |
| Example I-24 | 500 | 100 |
| Example I-27a | 500 | 83 |
| Example I-27b | 500 | 100 |

Example No 5

*Tetranychus* Test, OP-Resistant (TETRUR Spray Treatment)

Solvents: 78 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) which are infested by all stages of the greenhouse red spider mite (*Tetranychus urticae*) are sprayed with a preparation of active compound of the desired concentration.

After the desired period of time, the effect in % is determined. 100% means that all spider mites have been killed; 0% means that none of the spider mites have been killed.

In this test, for example, the following compounds of the Preparation Examples show good activity: see table.

| Example | Active compound concentration in g/ha | Kill rate in % after 6 days |
| --- | --- | --- |
| Example I-12b | 500 | 90 |

Example No. 6

*Myzus persicae* Test, Hydroponic Treatment (MYZUPE sys.)

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

The preparation of active compound is mixed with water. The stated concentration refers to the amount of active compound per volume unit of soil (mg/l=ppm). The treated water is filled into containers housing a pea plant (*Pisum sativum*) which is then infected with the green peach aphid (*Myzus persicae*).

After the desired period of time, the kill in % is determined. 100% means that all aphids have been killed; 0% means that none of the aphids have been killed.

In this test, for example, the following compounds of the Preparation Examples show good activity: see table.

| Example | Active compound concentration in ppm | Kill rate in % after 6 days |
| --- | --- | --- |
| Example I-2 | 20 | 100 |
| Example I-7 | 20 | 100 |
| Example I-9 | 20 | 100 |

Example No. 7

*Aphis gossypii* Test (APHIGO)

Solvent: 7 parts by weight of dimethylformrnamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed.

In this test, for example, the following compounds of the Preparation Examples show good activity: see table.

| Example | Active compound concentration in ppm | Kill rate in % after 6 days |
| --- | --- | --- |
| Example I-2 | 20 | 95 |
| Example I-7 | 100 | 95 |
| Example I-9 | 100 | 90 |

Example No. 8

*Lucilia cuprina* Test (LUCICU)

Solvent: dimethyl sulphoxide

To produce a suitable preparation of active compound, 1 part by weight of active compound is mixed with the stated amount of water and the concentrate is diluted with water to the desired concentration.

Containers containing horse meat treated with the preparation of active compound of the desired concentration are populated with *Lucilia cuprina* larvae.

After the desired period of time, the kill in % is determined. 100% means that all larvae have been killed; 0% means that none of the larvae have been killed.

In this test, for example, the following compounds of the Preparation Examples show good activity: see table.

| Example | Active compound concentration in ppm | Kill rate in % after 2 days |
|---|---|---|
| Example I-2 | 100 | 100 |
| Example I-6 | 100 | 100 |
| Example I-9 | 100 | 80 |

Example No. 9

*Aphis gossypii* Test (APHIGO)

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by spraying with the preparation of active compound at the stated concentration.

After the desired period of time, the kill in % is determined. 100% means that all animals have been killed; 0% means that none of the animals have been killed.

In this test, for example, the following compounds of the Preparation Examples show good activity: see table

| Example | Active compound concentration in g/ha | Kill rate in % after 7 days |
|---|---|---|
| Example I-2 | 12 | 85 |

The invention claimed is:

1. A bicyclic enaminocarbonyl compound of formula (I)

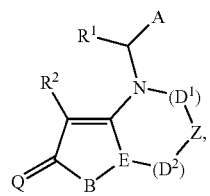

(I)

in which

A represents a radical selected from the group consisting of 6-chloropyrid-3-yl; 6-bromopyrid-3-yl; 6-methylpyrid-3-yl; 6-trifluoromethylpyrid-3-yl; 2-methylpyrimidin-5-yl; 2-chloropyrimid-5-yl; 1H-pyrazol-4-yl, which is optionally substituted in the 1-position by methyl or ethyl and in the 3-position by chlorine; 1H-pyrazol-5-yl; 3-methylpyrazol-5-yl; 2-bromo-1,3-thiazol-5-yl; 2-chloro-1,3-thiazol-5-yl; isoxazol-5-yl, which is optionally substituted in the 3-position by methyl, ethyl, chlorine or bromine; 3-methyl-1,2,4-oxadiazol-5-yl; 1-methyl-1,2,4-triazol-3-yl; 1,2,5-thiadiazol-3-yl; 5-fluoro-6-chloropyrid-3-yl; 5,6-dichloropyrid-3-yl; 5-bromo-6-chloropyrid-3-yl; 5-fluoro-6-bromopyrid-3-yl; 5-chloro-6-bromopyrid-3-yl; 5,6-dibromopyrid-3-yl; 5-methyl-6-chloropyrid-3-yl; 5-methyl-6-iodopyrid-3-yl; and 5-difluoromethyl-6-chloropyrid-3-yl, B represents oxygen or methylene, E represents CH or C-alkyl, $D^1$-Z-$D^2$ as a group represent —$CH_2$—$CH_2$—, —HC=CH—, —$CH_2$—$CH_2$—$CH_2$—, —$CH_2$—C(=$CH_2$)—$CH_2$—, —$CH_2$—CO—$CH_2$—, —$CH_2$—CH(OH)—$CH_2$—, —$CH_2$—$CF_2$—$CH_2$—, —$CH_2$—CHF—$CH_2$—, —$CH_2$—CHCl—$CH_2$—, —CH=CH—$CH_2$—, —$CH_2$—$CH_2$—CH=, —$CH_2$—$CH_2$—CH(OH)—, —$CH_2$—CH($CH_3$)—$CH_2$—, —$CH_2$—$CH_2$—$CH_2$—$CH_2$—, —$CH_2$—CH=CH—$CH_2$—, —$CH_2$—O—$CH_2$—, —$CH_2$—$CH_2$—O—, —$CH_2$—N($CH_3$)—$CH_2$—, —$CH_2$—$CH_2$—N($CH_3$)—, or —$CH_2$—S—$CH_2$—, $R^1$ represents hydrogen, $R^2$ represents hydrogen, fluorine, or chlorine, and Q represents oxygen.

2. A composition, comprising at least one compound of formula (I) according to claim 1 and a customary extender and/or surfactant.

3. A method for controlling pests, comprising allowing a compound of formula (I) according to claim 1 to act on the pests and/or a habitat thereof.

4. A composition for controlling pests comprising a compound according to claim 1.

5. A method for controlling pests comprising allowing a composition according to claim 2 to act on the pests and/or a habitat thereof.

6. The bicyclic enaminocarbonyl compound of the formula (I) according to claim 1 wherein A represents a radical selected from the group consisting of 6-chloropyrid-3-yl, 6-bromopyrid-3-yl, 2-chloropyrimid-5-yl, 5-fluoro-6-chloropyrid-3-yl, 5,6-dichloropyrid-3-yl, 5-fluoro-6-bromopyrid-3-yl, and 2-chloro-1,3-thiazol-5-yl, B represents oxygen, and $D^1$-Z-$D^2$ as a group represents —$CH_2$—$CH_2$—$CH_2$—, —$CH_2$—C(=$CH_2$)—$CH_2$—, —$CH_2$—C($CH_3$)—$CH_2$—, —$CH_2$—$CH_2$—$CH_2$—$CH_2$—, —$CH_2$—CH=CH—$CH_2$—, —$CH_2$—O—$CH_2$—, —$CH_2$—$CH_2$—O—, —$CH_2$—CHF—$CH_2$—, —$CH_2$—CHCl—$CH_2$—, —CH=CH—$CH_2$—, —$CH_2$—$CH_2$—CH=, or —$CH_2$—$CH_2$—CH(OH)—.

7. A composition comprising at least one bicyclic enaminocarbonyl compound of the formula (I) according to claim 6 and a customary extender and/or surfactant.

8. A method for controlling pests, comprising allowing a compound of the formula (I) according to claim 6 to act on the pests and/or habitat thereof.

9. A method for controlling pests comprising allowing a composition according to claim 7 to act on the pests and/or their habitat thereof.

10. A composition for controlling pests comprising a compound according to claim 6.

11. The bicyclic enaminocarbonyl compound of the formula (I) according to claim 1 wherein A represents 6-chloropyrid-3-yl or 2-chloro-1,3-thiazol-5-yl, B represents oxygen or methylene, E represents CH or C-alkyl, $D^1$-Z-$D^2$ represents —$CH_2$—$CH_2$—$CH_2$—, —$CH_2$—C(=$CH_2$)—$CH_2$—, —$CH_2$—CO—$CH_2$—, —$CH_2$—CH(OH)—$CH_2$—, —$CH_2$—CHF—$CH_2$—, —$CH_2$—CHCl—$CH_2$—, —CH=CH—$CH_2$—, —$CH_2$—$CH_2$—CH=, —$CH_2$—$CH_2$—CH(OH)—, —$CH_2$—CH($CH_3$)—$CH_2$—, —$CH_2$—$CH_2$—$CH_2$—$CH_2$—, —$CH_2$—CH=CH—$CH_2$—, —$CH_2$—O—$CH_2$—, or —$CH_2$—$CH_2$—O—, $R^1$ represents hydrogen, $R^2$ represents hydrogen, fluorine, or chlorine, and Q represents oxygen.

12. A composition comprising at least one bicyclic enaminocarbonyl compound of the formula (I) according to claim 11 and a customary extender and/or surfactant.

13. A method for controlling pests, comprising allowing a compound of the formula (I) according to claim 11 to act on the pests and/or habitat thereof.

14. A method for controlling pests comprising allowing a composition according to claim 12 to act on the pests and/or their habitat thereof.

15. A composition for controlling pests comprising a compound according to claim 11.

* * * * *